(12) United States Patent  
Paxson et al.

(10) Patent No.: US 8,543,337 B2  
(45) Date of Patent: Sep. 24, 2013

(54) BLOCK DIAGRAM EXPLORER IN A METHOD AND APPARATUS FOR INTEGRATED MODELING, SIMULATION AND ANALYSIS OF CHEMICAL AND BIOLOGICAL SYSTEMS

(75) Inventors: Ricardo E. Paxson, Boston, MA (US); Melissa J. Pike, Milford, MA (US); Joseph F. Hicklin, Upton, MA (US); Roy Lurie, Hopkinton, MA (US); Edward Whittington Gulley, Watertown, MA (US)

(73) Assignee: The MathWorks, Inc., Natick, MA (US)

( * ) Notice: Subject to any disclaimer, the term of this patent is extended or adjusted under 35 U.S.C. 154(b) by 1533 days.

(21) Appl. No.: 11/408,723

(22) Filed: Apr. 21, 2006

(65) Prior Publication Data

US 2007/0250299 A1    Oct. 25, 2007

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
None
See application file for complete search history.

(56) References Cited

U.S. PATENT DOCUMENTS 6,658,429 B2 * 12/2003 Dorsett, Jr. .................... 707/708
7,502,780 B2 *  3/2009 Thorpe ............................. 1/1

FOREIGN PATENT DOCUMENTS

| | | | |
|---|---|---|---|
| EP | 1494141 A2 | | 1/2005 |
| EP | 1566761 A2 | | 8/2005 |
| WO | WO 96/22575 | * | 7/1996 |
| WO | WO-00/49540 A1 | | 8/2000 |
| WO | WO-2004/081862 A2 | | 9/2004 |
| WO | WO 2006/036008 | * | 4/2006 |
| WO | WO-2006/036008 A1 | | 4/2006 |

OTHER PUBLICATIONS

International Search Report for Application No. PCT/US2007/009889, dated Jan. 25, 2008.
European Office Action for Application No. 07776059.3, dated Mar. 3, 2009.

* cited by examiner

*Primary Examiner* — Larry D Riggs, II
(74) *Attorney, Agent, or Firm* — Nelson Mullins Riley & Scarborough LLP

(57) ABSTRACT

A system for modeling, simulating and analyzing chemical and biochemical reactions includes a modeling environment for constructing a model of a chemical or biochemical system comprising a plurality of chemical reactions. The system also includes a simulation engine accepting as input said constructed model of the chemical or biochemical system and generating as output an expected result. The modeling environment includes a block diagram explorer for displaying a block diagram in a graphical user interface describing the system as a hierarchical network of interconnected blocks. Each block represents a species participating one of the chemical reactions or one of said chemical reactions in the system. The block diagram explorer allows for a user to manipulate and modify the graphical parameters of the block diagram representation to provide insight into the functionality and operation of the system being modeled.

28 Claims, 15 Drawing Sheets

Reaction Table

| Reaction | Kinetic Law | Parameter | Reversible |
|---|---|---|---|
| s70 + RNAP -> s70:RNAP | Mass Action | K | true |
| pg + s70:RNAP -> s70:RN... | Mass Action | K | true |
| s70:RNAP:pg -> mRNA_32 | Mass Action | K | true |
| mRNA_32 -> null | Mass Action | K | false |
| mRNA_32 -> s32 | Mass Action | K | true |
| s32 -> null | Mass Action | K | false |
| s32 + RNAP -> s32:RNAP | Mass Action | K | true |
| ph + s32:RNAP -> s32:RN... | Mass Action | K | true |
| s32:RNAP:ph -> mRNA_DnaK | Mass Action | K | true |
| mRNA_DnaK -> null | Mass Action | K | false |
| mRNA_DnaK -> DnaK | Mass Action | K | true |
| DnaK -> null | Mass Action | K | false |
| s32 + DnaK -> s32:DnaK | Mass Action | K | true |
| Punfolded + DnaK -> Punfo... | Mass Action | K | true |
| Punfolded:DnaK + Pfolded... | Mass Action | K | true |
| Pfolded -> Punfolded | Mass Action | K | true |
| s32:RNAP:ph -> mRNA_FtsH | Mass Action | K | false |
| mRNA_FtsH -> null | Mass Action | K | true |
| mRNA_FtsH -> FtsH | Mass Action | K | false |
| FtsH -> null | Mass Action | K | true |
| s32:RNAP:ph -> mRNA_HslVU | Mass Action | K | false |
| mRNA_HslVU -> null | Mass Action | K | true |
| mRNA_HslVU -> HslVU | Mass Action | K | false |
| HslVU -> null | Mass Action | K | true |
| S32:RNAP:ph -> mRNA_Pro... | Mass Action | K | true |

Species Table

| Name | Initial Amount | Constant |
|---|---|---|
| DnaK | 0 | false |
| FtsH | 0 | false |
| HslVU | 0 | false |
| Pfolded | 17800 | false |
| Protease | 0 | false |
| Punfolded | 0 | false |
| Punfolded:DnaK | 0 | false |
| RNAP | 1337.6174 | false |
| mRNA_DnaK | 0 | false |
| mRNA_FtsH | 0 | false |
| mRNA_HslVU | 0 | false |
| mRNA_Protease | 0 | false |
| mRNA_s32 | 0 | false |
| null | | |

Models:
- heatshock
  - Reactions
  - Species
    - > Dnak
    - > FtsH
    - > HslVU
    - > Pfolded
    - > Protease
    - > Punfolded
    - > Punfolded Dnak
    - > RNAP
    - > mRNA_Dnak
    - > mRNA_FtsH
    - > mRNA_HslVU
    - > mRNA_Protease
    - > mRNA_s32
    - > null
    - > pg
    - > ph
    - > s32
    - > s70
    - > s32:Dnak
    - > s32:RNAP
    - > s32:RNAP:ph
    - > s70:RNAP
    - > s70:RNAP:pg

*Fig. 2B*

BLOCK DIAGRAM EXPLORER IN A METHOD AND APPARATUS FOR INTEGRATED MODELING, SIMULATION AND ANALYSIS OF CHEMICAL AND BIOLOGICAL SYSTEMS

FIELD OF THE INVENTION

The present invention relates to simulation tools and, in particular, to an improved environment for modeling chemical and biochemical systems.

BACKGROUND OF THE INVENTION

The development of new drug targets by the pharmaceutical industry is time-consuming and expensive because a large number of possible targets need to be tested before the molecule or compound with the desired properties is found or formulated. Along the same argument, but not for the purpose of new drug development, are the activities or synthetic biology. Here, biological entities are designed to perform a particular function. A particular example of this case is the development of biological nanomachines that might for example be used as programmed drug delivery systems. (See J. Panyam, V. Labhasetwar, Biodegradable nanoparticles for drug and gene delivery to cells and tissue., Advanced Drug Delivery Reviews, 55 (2003) 329-347.) As in drug discovery efforts, the formulation of a compound with desired properties is difficult due to the large variety of possible targets and the even larger context or system in which they must perform their function. Currently much of the work done to investigate the properties of these compounds is done in a wet-lab requiring many tedious and error prone experiments.

Development of chemical substances and nanomachinery, in addition to being time-consuming, can generate potentially dangerous intermediate substances. For example, a molecule used as transport for a drug in a drug delivery system could by its mere presence in the organism, stimulate the overproduction of some other protein. The overexpressed protein could act as a lethal toxin for the organism. Another possible complication is that the nanomachinery itself may mutate over time and either lose its original function or worse adversely interfere with the viability of the organism.

Another problem facing the drug development activity is that, due to the cumbersome nature of experimental data collection, it is typical to limit experiments by narrowing the range of tested inputs and in general isolating the subsystem of interest. This limitation allows for the possibility that new drugs have unforeseen side-effects.

Moreover, current methods of obtaining data for biological processes are even more time-consuming than those associated with chemical processes, because the latter generally require laboratory experiments that lead to animal experiments and clinical trials. From these trials and experiments, data are obtained which, again, usually focus on a very narrow part of the biological system. Only after numerous costly trial-and-error clinical trials and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug. While conclusions may be drawn by assimilating experimental data and published information, it is difficult, if not impossible, to synthesize the relationships among all the available data and knowledge.

The various challenges faced by the aforementioned activities in chemical and biochemical research make it desirable to have software and methods for modeling, simulating, and analyzing biological processes in-silico rather than in-vitro or in-vivo. The goal of this approach is to provide a more comprehensive view of these biological systems prior to costly experiments and to clinical trials thereby reducing the search space for drug targets and useful nanoparticles.

The simulation of biological systems requires the use of many modes of computation such as continuous time, discrete step, hybrid, particle level among others. The need for these arises from the various simplifying assumptions made in order to make the problem tractable using today's computer technology and resources. At the most basic level, the particle based approach, every molecule in a cell is accounted for individually. Given the number of molecular components in a cell this approach is prohibitively expensive unless it is used for small relatively small number of molecules in the overall system. Approximations can be made which result in a significant reduction in the computational cost. One class of simplifications groups like-molecules and treats the entire group as one variable. This approach allows the development of probabilistic methods and well as differential ones, which are much less expensive in terms of computational cost. In effect, there is a continuum of methods varying from high fidelity, computationally intensive methods to approximate and less expensive methods. Hybrid solvers are those that mix one or more of these methods to optimize the use of computational resources while achieving a high level of fidelity.

One such method which accounts for the random nature of molecular interactions is called a stochastic simulator. A stochastic simulator may be used to simulate the time varying behavior of a collection of chemically interacting molecules in a chemical or biological system. In this case, the simulator maintains a list of reactions in the chemical or biological system that "could" take place and moves the state of the system forward through time in a two-step process. First, the simulator determines which reaction in the list of reactions will be the next to occur, and the time at which that reaction will occur. Second, the simulator updates the system to account for a reaction occurrence by adjusting the quantities of each type of molecule as specified by the stoichiometry of the reaction. This process is repeated iteratively as the system is marched forward in time. (See D. Gillespie, J. Phys. Chemistry, 81, 25 (1977).)

Current modeling and simulation environments allow users to create a map of molecular interactions for a system in a block diagram format. The size of these maps is potentially extremely large, depending on the size and complexity of the system being modeled. However, users are limited to passive viewing of the map without allowing for further investigation into the dynamics of the system.

SUMMARY OF THE INVENTION

The present invention provides a modeling and simulation environment for biological and/or chemical systems. The modeling and simulation environment includes a modeling environment for constructing a model of a chemical or biochemical system comprising a plurality of chemical reactions, in addition to other mathematical expressions that may define the system. The system also includes a simulation engine accepting as input the constructed model of the chemical or biochemical system and generating as output time-course behavior of the system.

The present invention may visualize molecular interactions in a biological or chemical system and enable users to investigate or explore into the dynamics of the system. The present invention may use simulation results as input for the automatic layout of the system. The present invention may also use user inputs to make manual organization and exploration of the system.

The present invention may allow for modification of the graphical layout of a graphical model of a biological or chemical system after creation. The modification of the graphical layout may cause the graphical attributes, such as position, color, shape, etc., of the model to be changed. The modification may alter the layout of the graphical model, or change the underlying model of the biological or chemical system to facilitate study of the system. The modification may be automatic or user-directed. The modification may be in response to a simulation of the graphical model, an analysis of the underlying model of the system or based on other parameters.

The modeling environment may provide a block diagram explorer for providing a graphical display of a model of a biological or chemical system and enabling manipulation of the graphical display. The modeling environment allows for construction of a map comprising a block diagram describing the system as a hierarchical network of interconnected blocks. Each block may represent a species participating in one of the chemical reactions or one of the chemical reactions in the system. The block diagram explorer includes user interface means for allowing a user to input instructions for modifying the graphical display. In response to user instructions, the modeling environment modifies the display accordingly. For example, a user can instruct the modeling environment to hide or split selected blocks, highlight selected blocks, show hidden blocks, join split blocks and perform other manipulations of the graphical representation of the system, without affecting the operation of the underlying model. The modeling environment may split the graphical representation of a selected object into a plurality of cloned blocks without actually creating a new object in the model. The modeling environment may also perform joining cloned blocks into a single representation.

According to a first aspect of the invention, a method of modeling a system comprising a plurality of chemical reactions in an electronic device is provided. The method comprises the steps of displaying a block diagram in a graphical user interface describing the system as a hierarchical network of interconnected blocks, each block representing a species participating one of the chemical reactions or one of said chemical reactions in the system and, in response to a user request, modifying a graphical parameter of a block of the block diagram.

According to another aspect of the invention, a method of modeling a system comprising a plurality of chemical reactions in an electronic device is provided, which comprises the steps of receiving an instruction from a user regarding a graphical parameter of a block diagram describing the system as a hierarchical network of interconnected blocks. Each block represents a species participating in one of the chemical reactions or one of said chemical reactions in the system. The method further comprises modifying the block diagram according to the user instruction.

According to another aspect of the invention, a system for improved modeling and simulation of a system that comprises a plurality of chemical reactions is provided. The system comprises a modeling component comprising a graphical user interface for accepting user commands and input to construct a model of the reaction system. The modeling component includes a block diagram explorer for displaying a block diagram in a graphical user interface describing the system as a hierarchical network of interconnected blocks, each block representing a species participating in one of the chemical reactions or one of said chemical reactions in the system, wherein the block diagram explorer receives a user instruction regarding the block diagram and processes the instruction to modify a graphical parameter of the block diagram. The system further comprises a simulation engine accepting as input said constructed model of the reaction system and generating as output dynamic behavior of the reaction system.

BRIEF DESCRIPTION OF THE FIGURES

The invention is pointed out with particularity in the appended claims. The advantages of the invention described above, and further advantages of the invention, may be better understood by reference to the following description taken in conjunction with the accompanying drawings, in which:

FIGS. 2A and 2B are screenshots depicting embodiments of a tabular modeling environment useful in connection with the present invention;

DETAILED DESCRIPTION OF THE INVENTION

The present invention facilitates modeling and analysis of a chemical or biological system. The present invention will be described below relative to an illustrative embodiment. Those skilled in the art will appreciate that the present invention may be implemented in a number of different applications and embodiments and is not specifically limited in its application to the particular embodiments depicted herein.

In an embodiment of the invention, a system for modeling, simulating and analyzing chemical and biochemical reactions includes a modeling environment for constructing a model of a chemical or biochemical system that includes a number of chemical reactions. The system also includes a simulation engine accepting as input said constructed model of the chemical or biochemical system and generating as output the dynamical behavior of the system as modeled. An analysis environment may communicate with the simulation engine and displays this result.

The modeling environment may provide a block diagram explorer for displaying the chemical or biological system in block diagram form as a hierarchical network of interconnected and interacting species and reactions. The block diagram explorer includes user interface means for allowing a user to manipulate the graphical characteristics of the block diagram representing the chemical or biological system. The ability to manipulate the graphical characteristics of the block diagram allows the user to perform additional analysis of the system from different perspectives.

Figure 1:
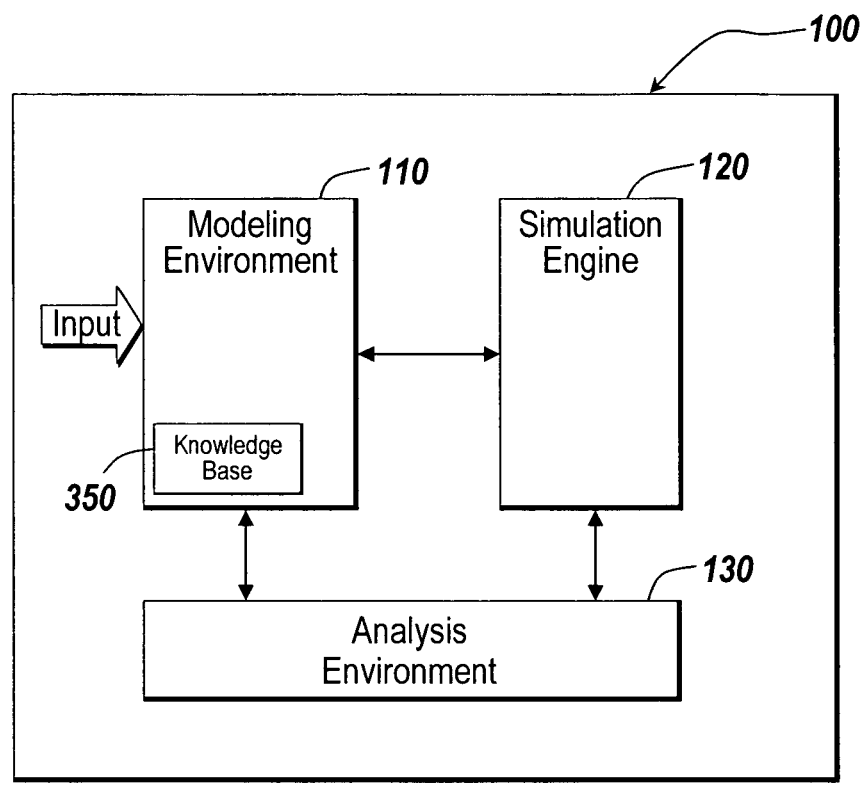
FIG. 1 is a block diagram of one embodiment of an integrated modeling, simulation and analysis environment.

Referring now to FIG. 1, a high-level block diagram of one embodiment of an integrated system for modeling, simulating, and analyzing chemical reactions and biological systems that include biological processes 100 is shown. As shown in FIG. 1, the system 100 includes a modeling component designated as a modeling environment 110 in the exemplary depiction of FIG. 1, a simulation engine 120, and an analysis environment 130. The simulation engine 120 communicates with the modeling environment 110. The simulation engine 120 receives models of chemical reactions or biological processes generated using the modeling environment 110. The simulation engine 120 communicates refinements to models created in the modeling environment 110. The analysis environment 130 is in communication with both the modeling environment 110 and the simulation engine 120. The analysis environment 130 may be used to perform various types of analysis directly on models created in the modeling environment 110. In addition, the analysis environment 130 may receive and process results from the simulation engine 120 representing the execution by the simulation engine 120 of a model produced in the modeling environment. In other words, the simulation engine 120 generates the dynamic behavior of the model and communicates at least some of this dynamic behavior to the analysis environment. The analysis environment 130 may provide refinements to a model in the modeling environment 110 and may provide parameters for use by the simulation engine 120 when executing a model. The interaction between the modeling environment 110, the simulation engine 120, and the analysis environment 130 will be discussed in more detail below.

The integrated system depicted in FIG. 1 may execute on a number of different computing platforms known in the art, such as, but not limited to, supercomputers, mainframe computers, minicomputers, clustered computing platforms, workstations, general-purpose desktop computers, laptops, and personal digital assistants.

The modeling environment 110 accepts input to create a model of the chemical or biochemical system to be simulated. In some embodiments, the modeling environment 110 accepts input contained in a file, such as a file in Systems Biology Markup Language (SBML). SBML is a standard for representing models of biochemical reaction networks, including metabolic networks, cell-signaling pathways, regulatory networks, and many others. In others of these embodiments, the file may be in HyperText Markup Language (HTML) format, Extensible Markup Language (XML) format, a proprietary markup language, or a text file in which fields are delimited by tabs or commas. Alternatively, the modeling environment 110 may accept input produced by a user via either a command-line interface or a graphical user interface.

The modeling environment may include a plurality of reaction objects for defining each reaction in the chemical or biochemical system to be simulated. Each reaction object may encapsulate all of the information about a particular reaction that may be used when modeling or simulating the reaction.

Figure 2A:
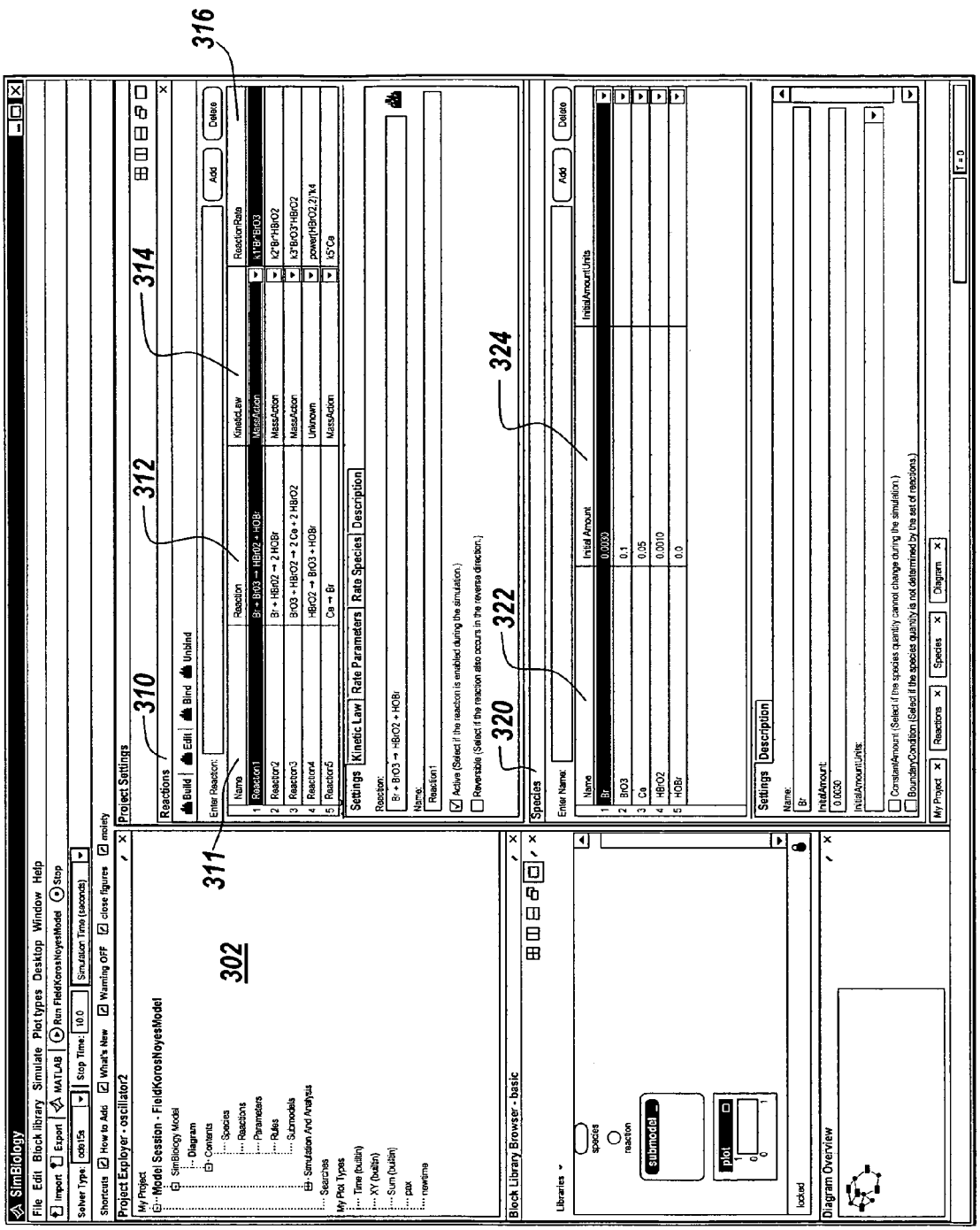

For example, a user can create a model of a chemical or biochemical system comprising a plurality of chemical reactions using a graphical user interface, as shown in FIGS. 2A and 2B. FIGS. 2A and 2B depict an embodiment of a tabular graphical user interface 300 that may be used to receive input manufactured by a user for creating a model. As shown in FIGS. 2A and 2B, the user interface may include a model pane 302. In the embodiment shown in FIGS. 2A and 2B, the model pane 302 lists one or more models in a tree structure familiar to users of computers operating under control of an operating system, such as the WINDOW operating system manufactured by Microsoft Corp. of Redmond, Wash., or another suitable operating system using graphical controls. In the particular embodiment depicted by FIG. 2A, the model pane 302 contains a model of a chemical reaction, indicated by the folder labeled "Model Session—FieldKorosNoyes-Model". That model contains subfolders: "Simbiology Model"; and "Simulation and Analysis." The "Simbiology Model" subfolder contains additional subfolders: "Diagram"; and "Content." The "Content" subfolder contains subfolders: "Reactions"; and "Species". The subfolders represent pieces of the modeled reaction. Each species is an entity that takes part in one or more of the reactions comprising the overall system. Other graphical user interface schemes may be used to present this information to the user of a system 100. In some embodiments, the model pane 302 may display a number of folders representing models. User selection of a particular folder causes the system to display a folder in the model pane 302 that represent pieces of the overall reaction, e.g., reactions, and species. In still other embodiments, each model and all components of all models may be displayed in the model pane 302 and each model may be associated with a "radio button." Selection of the radio button associates with a model causes that model and its constituents to be actively displayed. In some of these embodiments, unselected models are displayed in grey type, or may have a transparent grey overlay indicating that they are not currently the active model.

Referring back to FIG. 2A, the illustrative graphical user interface 300 also includes a reactions pane 310, and a species pane 320. The reactions pane 310 is associated with the "Reactions" folder displayed in the model pane 302. Similarly, the species table 320 is associated with the "Species" folder displayed in the model pane 302. In some embodiments, collapsing the associated folder causes the table to not be displayed. The respective tables may be displayed in their own graphical user interface window, rather than in the same window as the graphical user interface 300, as shown in FIG. 2A.

The reactions pane 310 lists each reaction present in a modeled biological process or chemical reaction. In the embodiment shown in FIG. 2A, the modeling environment 300 displays reactions present in the Field-Koros-Noyes model of the Belousov-Zhabotinsky reaction and includes four columns: a name column 311, a reaction column 312, a kinetic law column 314, and a reaction rate column 316. Each row of the reactions pane 310 corresponds to a particular reaction. The number and format of columns displayed by the reaction table may be selected by the user. In other embodiments, the modeling environment 110 may select the number and format of columns to display based on the type of reaction selected by the user.

Referring back to the embodiment shown in FIG. 2A, the name column 311 displays the name representing each reaction, and the reaction column 312 displays a reaction represented in an abstract format, e.g., Ce→Br. In other embodiments, the reaction may be represented as a differential equation, in stochastic format, or as a hybrid of two or more of these formats. In some embodiments, the reactions pane includes a column identifying modifiers of the reaction. For example, some reactions can be catalyzed by a substance. This may be represented in the tabular format as Ce-m(s)→Br, meaning that the presence of the species "s" accelerates the conversion of Ce into Br.

In the embodiment shown in FIG. 2A, the reactions pane 310 also includes a kinetic law column 314 which identifies the kinetic law the identified reaction follows. The kinetic law column 314 may indicate whether the identified reaction follows the Law of Mass Action or "Michaels-Menten".

Still referring to the embodiment shown in FIG. 2A, the reactions pane 310 includes a reaction rate column 316, which identifies the reaction rate expression of the identified reaction. In the embodiment shown in FIG. 2A, the reaction rate associated with the Ce→Br reaction is "Ce*k5," meaning that Ce is consumed at a rate controlled by the parameter "k5" and the amount of Ce present. In the embodiment shown in FIG. 2A, the reaction rate expressions are listed in the reaction rate column 316. In some embodiments, the reactions pane 310 includes a column identifying the units in which the reaction rates are expressed, e.g., 1/seconds, 1/(moles*seconds), etc.

In some embodiments the reactions pane 310 may include a column identifying dynamics of the reaction, e.g., "fast" or "slow." In some of these embodiments, the rapidity with which a reaction occurs is identified on a scale of 1 to 10. In still other embodiments, the user may be presented with a slide control that allows the rapidity of various reactions to be set relative to one another. In still further embodiments, the reactions pane 310 may include a column for annotations or notes relating to the reaction.

The modeling environment 300 shown in FIG. 2A also displays a species pane 320 for defining the entities that take part in the reactions listed in the reactions pane 310. In the embodiment shown in FIG. 2A, the species pane 320 includes a name column 322, an initial amount column 324, and an initial amount unit column 326. The species pane depicts the initial conditions and amounts of material used in the modeled biological process or chemical reaction. Thus, in the embodiment shown in FIG. 2A, the modeled biological process begins with 0.003 molar units of bromine, i.e., 0.003 multiplied by Avrogado's number. The initial amount unit column 326 may identify the units (e.g., moles, molecules, liters, etc.) for the amount of the species. In other embodiments the species pane 320 includes other columns identifying whether a particular species is an independent variable in the model (i.e., whether the species is an input to the system), a column for annotations, or a column for notes.

In some embodiments, the modeling environment 300 accepts as input a file in a markup language, such as SBML, and converts that file into a graphical display of the sort depicted in FIG. 2A. For example, one representation of the Field-Koros-Noyes model of the Belousov-Zhabotinsky reaction in markup language that corresponds to the particular embodiment shown in FIG. 2A is shown in Appendix A to this document.

For example, a process may be provided that uses the information embedded in the tags of the markup language file, e.g., <reaction name="Reaction5" Kinetic Law="MassAction">, to generate the tabular form of the model shown in FIGS. 2A and 2B. In some of these embodiments, a web browser may be modified to parse files containing models written in markup language in order to create the tabular form of the model shown in FIGS. 2A and 2B. In other embodiments, a process may accept the model as input and generate as output code that is directly executable on a processor, such a code written in the C programming language.

The model of a chemical or biochemical reaction created in the modeling environment may be converted into executable code. Conversion of a model into executable code allows the executable code to be transmitted to multiple computers via a network for execution on those computers. In these embodiments computers may be connected via a number of network topologies including bus, star, or ring topologies. The network can be a local area network (LAN), a metropolitan area network (MAN), or a wide area network (WAN) such as the Internet.

In these embodiments, a master server parses a model written in markup language. The model may be retrieved from a hard disk or from another computer accessed via a network connection. In other embodiments, the model is input by a user using a tabular user input such as the one shown in FIGS. 2A and 2B or graphical user interfaces such as the one shown in FIGS. 3A and 3B. The master server parses the model to produce executable code. The executable code produced by the master server may be compiled code, such as code written in C, C+, C++, or C# and compiled to run on a target platform or the executable code produced by the master server may be a in a bytecode language such as JAVA. In some embodiments, the executable code is transmitted to one or more computers via a network connection. The one or more computers execute the code representing the model and return the generated result to the master server. The master server may store the retrieved results for later analysis. In some embodiments, the master server displays a graphical representation of each of the received results. In one embodiment, this technique is used to conduct Monte Carlo type analysis. In certain of these embodiments, the master server may collect and display each data point received and display each data point graphically in real-time.

FIG. 2B depicts in tabular form reactions for simulating the *E. Coli* heat shock response model according to an illustrative embodiment of the invention. As described above in connection with FIG. 2A, the upper table displays the various reactions involved in transcription and translation of the heat shock proteins as well as the interactions of heat shock proteins with unfolded (or denatured) proteins. As depicted in FIG. 2B, all reactions in the *E. Coli* heat shock response model have mass action kinetics and some are reversible, while some are not. Another method of representing chemical or biochemical reactions is by way of a block diagram, as described in detail below.

Figure 3A:
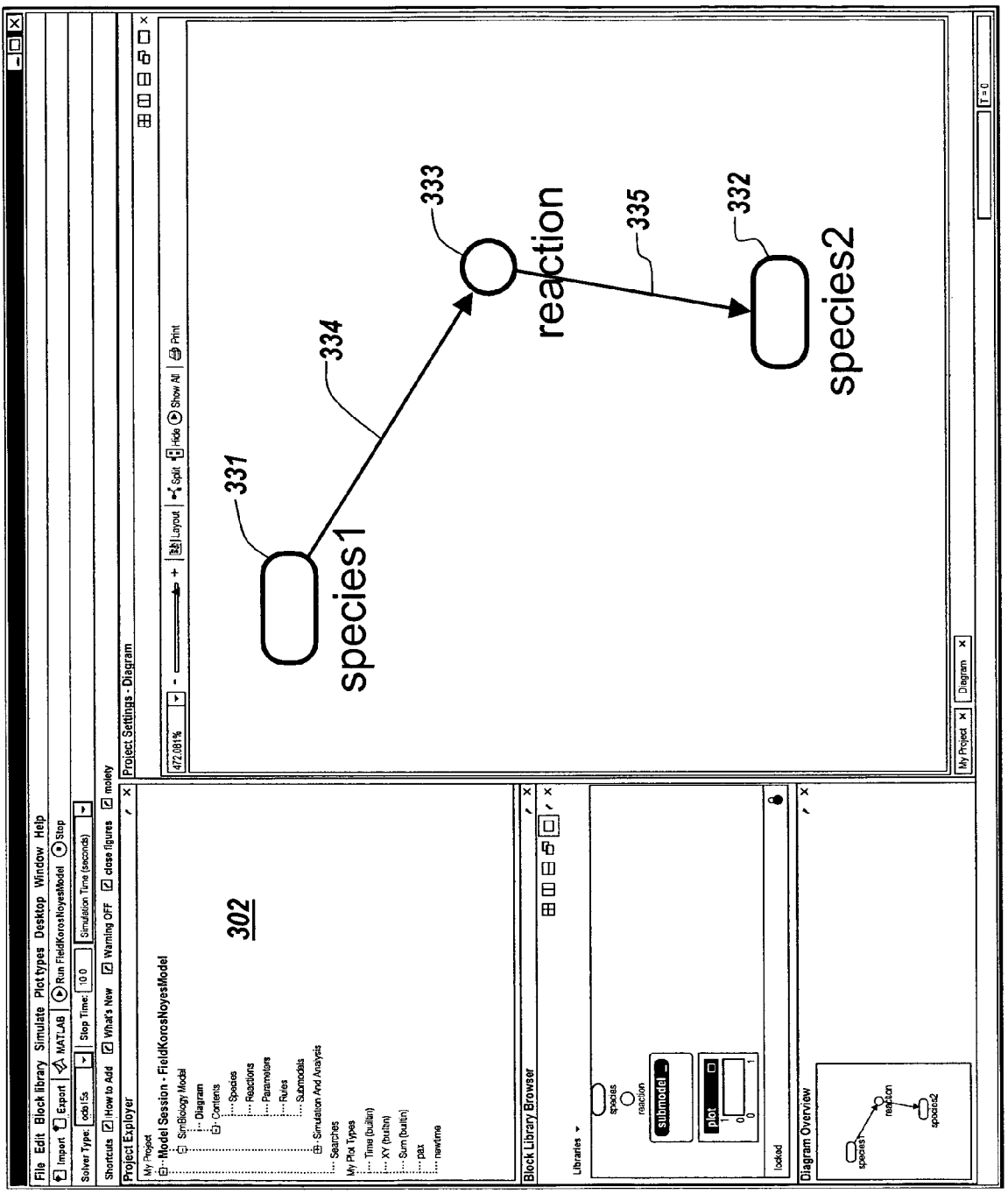
FIGS. 3A and 3B are screenshots of one embodiment of a graphical user interface that facilitates construction of block diagram representations of chemical reactions or biological processes.
Figure 3B:
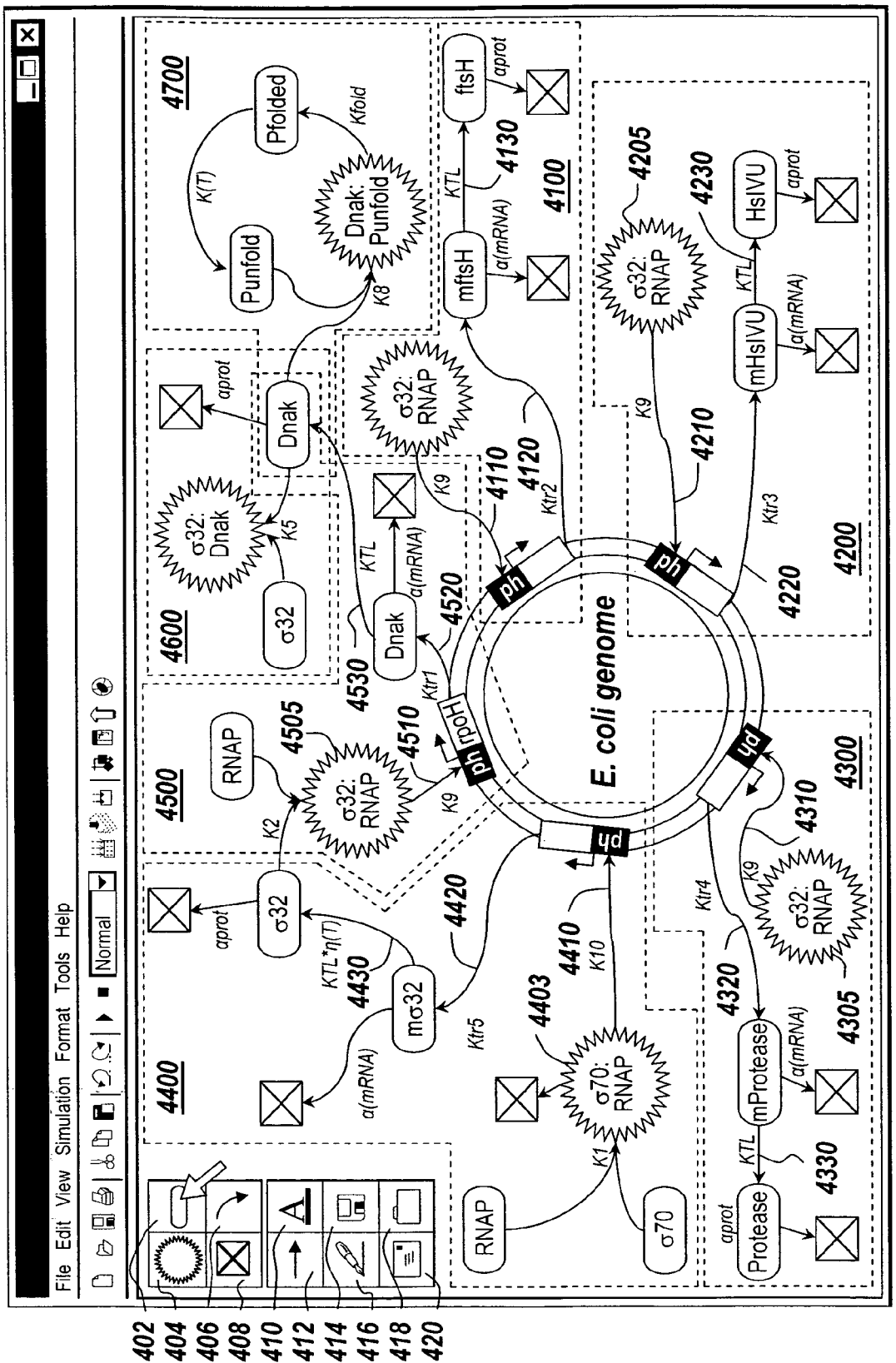

In still other embodiments, the modeling environment 300 allows a user to represent a biological process or chemical reaction as a block diagram. FIGS. 3A and 3B depict embodiments of a block diagram modeling environment. A block diagram editor within the modeling environment 300 allows users to perform such actions as draw, edit, annotate, save, and print out block diagram representations of dynamic systems. Blocks are the fundamental mathematical elements of a classic block diagram model. The block diagram editor is generally a graphical user interface (GUI) component that allows drafting of block diagram models representing a chemical or biochemical reaction by a user. FIG. 3A depicts an embodiment of a GUI 330 for a block diagram editor. In the embodiment shown in FIG. 3A, a user may build a model using various block tools and wiring line connection tools.

The user may use pre-defined blocks 331 and 332 to represent the species participating in the reactions. The user may also use different types of blocks 333 to represent the reactions in the system. The user may connect these blocks using directed lines 334 and 335 in the model's window. The block diagram editor will be described below in more detail with reference to FIG. 3B.

In the embodiment depicted in FIG. 3B, a block diagram showing heat shock reaction in E. Coli bacteria is under construction. As is well known, heat shock response in E. coli is a protective cellular response to heat-induced stress. Elevated temperatures result in decreased E. coli growth, in large part, from protein unfolding or misfolding. The heat shock response, via heat shock proteins, responds to heat induced stress by refolding proteins via chaperones or by degrading nonfunctional proteins via proteases.

The block diagram shown in FIG. 3B depicts the expression of five particular gene sequences involved in the heat shock response. In part, FIG. 3B depicts pathways 4100, 4200, 4300 for the expression of proteases involved in heat shock response. Pathways 4100, 4200, 4300 represent the expression of heat shock proteins ftsH, Hs1VU and other proteases, respectively. The pathways 4100, 4200, 4300 are activated by the interaction 4105, 4205, 4305 of $\sigma^{32}$ with RNA polymerase at the promoter of the respective sequence. Each pathway 4100, 4200, 4300 depicts the transcription 4120, 4220, 4320 of the mRNA mediated 4110, 4210, 4310 by the $\sigma^{32}$ and RNA polymerase interaction 4105, 4205, 4305 at the promoter and the subsequent translation 4130, 4230, 4330 of the protease. The heat shock proteases, including ftsH and Hs1VU, serve to degrade proteins rendered nonfunctional by heat stress. Similarly, the diagram depicts the pathways 4400, 4500 involved in the expression of the heat shock proteins $\sigma^{70}$ and DnaK, respectively. The expression of the $\sigma^{32}$ protein is activated 4410 by the interaction 4403 of $\sigma^{70}$ and RNA polymerase at the promoter. The $\sigma^{32}$ mRNA is transcribed 4420 and, subsequently, $\sigma^{32}$ is translated 4430. In a closely related pathway 4500, the heat shock protein DnaK is translated. The interaction 4505 of $\sigma^{32}$ and RNA polymerase at the promoter activate 4510 the transcription 4520 of DnaK mRNA and, subsequently, the translation 4530 of DnaK. DnaK, in turn, may either interact 4600 with $\sigma^{32}$ so as to stabilize $\sigma^{32}$ or, alternatively, may refold 4700 the proteins unfolded by heat stress.

In some of these embodiments, the modeling environment includes two classes of blocks, non-virtual blocks and virtual blocks. Non-virtual blocks are elementary dynamic systems, such as the $\sigma^{32}$ and RNA polymerase interaction 4105, 4205, 4305. A virtual block may be provided for graphical organizational convenience and plays no role in the definition of the system of equations described by the block diagram model. For example, in the block diagram of the heat shock mechanism in E. Coli bacteria depicted in FIG. 3B, gene transcription mediated by σ32 to produce proteins, represented by 4100, 4200, and 4300, may be represented as a single, virtual block. In this case the virtual block adds hierarchy to a model for the purpose of improving the readability of models.

FIG. 3B depicts an embodiment of a GUI for a block diagram editor that features a floating element palette. In the embodiment shown in FIG. 3B, the GUI tools include various block tools 402, 404, 408, various wiring line connection tools 406, 412, an annotation tool 416, formatting tool 410, a save/load tool 414, a notification tool 420 and a publishing tool 418. The block tools 402, 404, 408 represent a library of all the pre-defined blocks available to the user when building the block diagram. Individual users may be able to customize this palette to: (a) reorganize blocks in some custom format, (b) delete blocks they do not use, and (c) add custom blocks they have designed. The blocks may be dragged through some human-machine interface (such as a mouse or keyboard) on to the window (i.e., model canvas). The graphical version of the block that is rendered on the canvas is called the icon for the block. There may be different embodiments for the block palette including a tree-based browser view of all of the blocks. In these embodiments, the floating element palette allows a user to drag block diagram elements from a palette and drop it in place on the screen. In some of these embodiments, there may also be a textual interface with a set of commands that allow interaction with the graphical editor. For example, dragging a polymerase block to the model may cause the system to prompt the user for the protein to be used in the polymerase reaction.

Using this textual interface, users may write special scripts that perform automatic editing operations on the block diagram. A user generally interacts with a set of windows that act as canvases for the model. There can be more than one window for a model because models may be partitioned into multiple hierarchical levels through the use of subsystems. In still other embodiments, only a textual interface may be provided for facilitating the user's construction of the block diagram.

The modeling environment 300 may also offer a variety of other GUI tools that improve the ability of users to build and manage large block diagrams. For example, wiring line connection tools 406, 412 allow users to draw directed lines that connect the blocks in the model's window. Connections may be added through various other mechanisms involving human-machine interfaces, such as the keyboard. The annotation tool 416 allows users to add notes and annotations to various parts of the block diagram. The formatting tool 410 enables users to perform various formatting operations that are generally available on any document editing tool. The save/load tool 414 allows a created block diagram model to be saved in a library or other suitable location for future use. A publishing tool 418 may be provided to enable the viewing of the block diagram as a document that can be published in any standard document formats (examples: PostScript, PDF, HTML, SBML, XML, SGML, SBML etc.). A notification tool 420 allows a user working on a block diagram to send a message to another user. In some embodiments, the notification tool 420 causes the current version of the block diagram, to be mailed to the specified user.

Those skilled in the art will also recognize that block-diagram packages offer scripting languages for writing out programs that automatically carry out a series of operations that would normally require interaction with the GUI, such as block addition, block deletion, starting and terminating execution, or modifying block attributes, etc.

The modeling environment 300 may also offer a variety of other GUI tools that improve the ability of users to build and manage large block diagrams. Examples of such GUIs include: (a) a Finder that helps find various objects such as blocks and lines within a block-diagram, (b) a Debugger that helps debug the execution of block-diagrams, (c) a Revision Control UI for managing multiple revisions of the block-diagram, and (d) a Profiler for viewing timing results while executing a block-diagram.

In some embodiments, the modeling environment 110 includes a knowledge base 350 that aids in construction of a model. In some of these embodiments, the knowledge base 350 contains models for various reactions, e.g. glycolysis. In these embodiments, when a user begins to input reactions consistent with a model for glycolysis, the knowledge base 350 may enter the remaining reactions for the user. Alternatively, the knowledge base 350 may offer different models of the reaction to the user. In some of these embodiments, the offered models represent the target reaction with varying levels of detail. In other embodiments, the knowledge base 350 may insert parameters or indications of reversibility for entered reactions. For example, the knowledge base 350 may specify a reaction distribution for determining a reaction time for a selected reaction. The knowledge base 350 may also provide assistance to a user inputting a block diagram representation of a chemical or biochemical reaction. For example, the knowledge base 350 may prevent a user manufactured by connecting blocks inconsistent with the modeled reaction. Examples of publicly-available databases that may be used to facilitate generation of models include the Swissprot database, NCBI, the Protein Data Bank, and KEGG. Alternatively, the user may provide private databases to act as a knowledge base 350 for facilitating creation of models.

In other embodiments the knowledge base 350 may be used to facilitate further or broader understanding of the modeled reaction. For example, referring to the block diagram representation of the heat shock reaction in E. Coli bacteria, the knowledge base 350 can be used to identify other reactions in the heat shock reaction that use, or are impacted by, σ70. Alternatively, the knowledge base 350 may identify other reactions for E. Coli in which σ70 plays a part, e.g., chemotaxis. The knowledge base 350 may overlay the different models of reactions so that the user can easily compare the difference between the models of reactions. In this way, a broader understanding of the functioning of E. Coli in various environments can be achieved.

In still other embodiments, the modeling environment 110 provides libraries from which blocks may be selected and included in a model. Models referenced by virtual or non-virtual blocks in a model, whether or not part of a library, are included in the model for execution. For embodiments in which executable code is generated, code representing the referenced models is also generated.

According to an embodiment of the invention, a system for modeling, simulating and analyzing chemical and biochemical reactions may facilitate interaction with a graphical representation of a chemical or biological system. A block diagram explorer within the modeling environment 300 may provide a graphical display of a model of a biological or chemical system comprising a plurality of chemical reactions.

Figure 4:
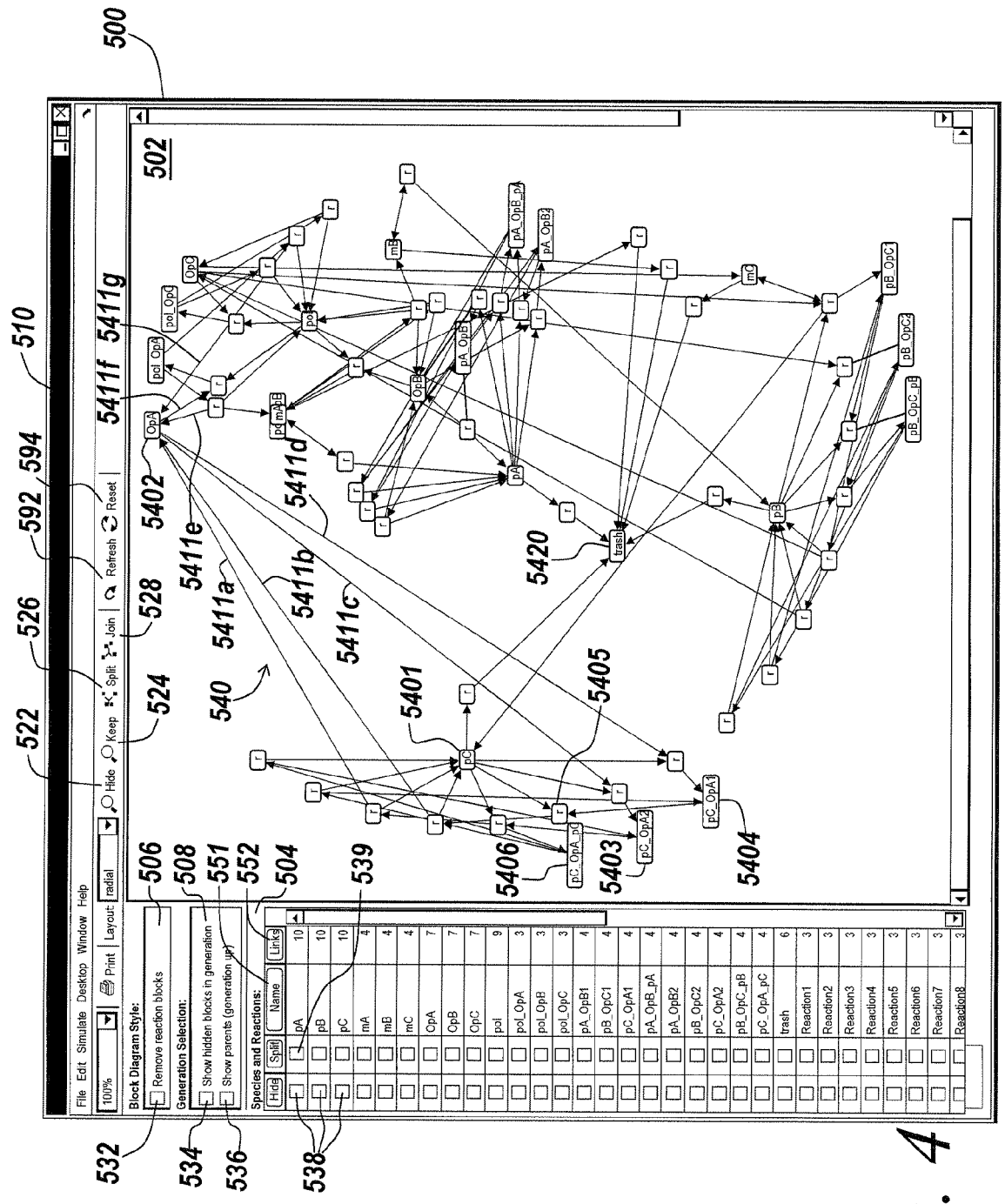
FIG. 4 is a screenshot of one embodiment of a block diagram explorer that displays a block diagram describing a biological or chemical system as a hierarchical network of interconnected blocks and allows a user to modify the block diagram.

An embodiment of a block diagram explorer 500 (view) is shown in FIG. 4. The block diagram explorer 500 allows for the user to perform further analysis of a model of a biological or chemical system after construction, and maps the hierarchical relationships and interactions between the different species and reactions that comprise the system being modeled. The block diagram explorer 500 includes a graphical user interface 510, comprising a block diagram pane 502 for displaying a block diagram 540 representing the system being modeled. The block diagram 540 graphically displays a model of a chemical or biological system as a hierarchical network of interconnected blocks. Each block in the block diagram 540 can represent a component of the model. For example, each block in the illustrative model represents either a reaction present in a modeled biological or chemical process/system or a species used in the modeled biological or chemical process/system. For a particular model defined using a tabular graphical user interface, such as the table 300 shown in FIGS. 2A and 2B, each block may corresponds to an entry in the reaction column 312 of the reaction table 310 or the species name column 322 in the species table 320 for that model. The block diagram explorer 500 thus provides a visual feedback regarding the relationship between the different components of the model, which can be useful to a user analyzing the model.

The illustrative block diagram 540 graphically illustrates the hierarchical connections between different species in the model and the reactions in the model that employ and/or produce each species. Each species is represented by a block having the species name therein, while each reaction is represented by a block having an "r" in the middle. Input arrows connect one or more species to a particular reaction that uses those species as an input. Output arrows also extend from a particular reaction, connecting the reaction to one or more species that are the products of that reaction.

Figure 5:
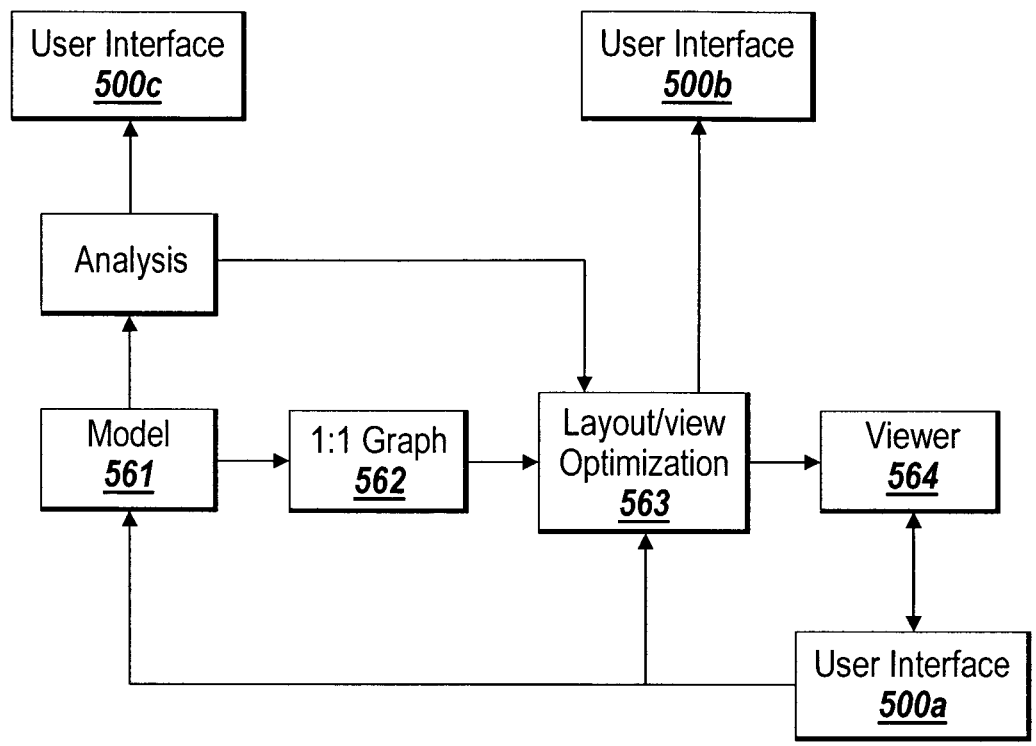
FIG. 5 illustrates components within the modeling environment that facilitate modification of graphical parameters of the model according to an embodiment of the invention.

FIG. 5 is a block diagram of components within the modeling environment 110 for generating the block diagram 540 from a model, allowing for a user to interact with the block diagram 540. The block diagram 540 may be produced with the assistance of software that determines where to position blocks on the screen, such as "graphviz" available from AT&T.

The modeling environment 110 takes a model 561, performs a 1:1 graphing on the model using a grapher 562, and passes the resulting graphed model to a layout/view optimizer 563. The layout/view optimizer 563 determines an optimal position for each of the blocks in the block diagram 540 based on selected rules and objectives. The layout/view optimizer 563 passes the position information to a viewer 564, which displays a graphical version of the block diagram 540. In addition, an analysis 565 can be performed on the model 561 from within the analysis environment 130.

To create the block diagram 540, a two-dimensional N×N matrix listing all of the species in the model is supplied to the optimizer 563, where N is the number of species in the model. Each column in the matrix correspond to one species, and each row corresponds to one species, such that the number of rows and number of columns each equal the number of species in the system and the diagonal entries across the matrix, i.e., the intersection of each species, are filled with zeros. The software in the optimizer processes the information in the matrix to produce a vector describing the two-dimensional position for each species in the matrix. Based on the vector, a technical computing environment, such as MATLAB, available from the Mathworks, Inc. of Natick, Mass., in the viewer 554 produces a block diagram of the model, such as the block diagram 540 illustrated in FIG. 4, with each species represented by a corresponding block in the selected position in the block diagram. The block diagram 540 may be displayed using any suitable means. In the illustrative embodiment, the block diagram is displayed in a pane 502 of a graphical user interface 500, illustrated as a block diagram explorer.

For example, in the left side portion of the illustrative model, the species pC, which is formed through various reactions and represented by block 5401, combines with the species OpA 5402 in a reaction represented by block 5403 to form the species pC_OpA1 5404, which in turn reacts with the species pC 5401 in a reaction represented by block 5405 to form the species pC_OpA_pC 5406. Various other reactions that comprise the overall system are also illustrated in the block diagram.

The illustrative block diagram explorer 500 also includes a list pane 504, which lists, in a "name" column 551, all the species and reactions for the selected model in a list or other suitable format. The illustrative list pane 504 further includes a "links" column 552, which lists, for each species or reaction block in the block diagram, the number of links connected to that block. The entries in the list pane 504 can be organized according to the name or the number of links or another selected format.

The selected rules and objectives employed by the layout/view optimizer 563 may be user-defined, automated or a combination of manual and automated. The rules and objectives may depend on the simulation of the model, an analysis performed on the model, or other parameters. For example, the results of the analysis 565 can be provided to the layout/view optimizer 553 to influence the layout of the block diagram of the model based on the analysis. Alternatively, the layout/view optimizer 563 may be designed to reduce clutter in the graphical model. The layout design can be based on multiple parameters.

One or more user interfaces 500a-c interface with the components of the system. In one embodiment, the user interface 500 interfacing with the viewer 564 is the block diagram explorer 500 shown in FIG. 4, which displays the graphical model produced by the viewer 564. Another user interface 500b interfaces with the layout/view optimizer 563, and allows a user to modify the rules and objectives used to determine the position of different components of the graphical model. Still another user interface 500c may interface with an analysis 565 performed on the model 561. The user interfaces 500a-c allow a user to interact with the graphical model and other components of the system. For example, the user interfaces may allow a user to transform the graphical model for certain purposes.

In contrast to prior viewers for viewing a graphical model, the viewer 564 does not provide a static display of a model, but rather a dynamic display. The display may be interactive with a user, allowing the user to modify the display characteristics, the underlying model, the analysis, or the algorithm used by the view optimizer 563 in response to the display on the view 564. The interaction may be made using the user interfaces, such as the block diagram explorer 500.

Alternatively, the display may be automatically transformed without user interaction. The display may be altered based on a simulation of the model, based on an analysis of the model or another basis. For example, based on the simulation, the view optimizer may put blocks with a lot of flux in the middle of the graphical model in the viewer, or the layout may be driven by time-varying simulation parameters.

The ability to manipulate the graphics of a graphical model of a biological or chemical system allows for insight into the structure and/or arrangement of the system.

For example, the user can selectively remove certain blocks from the block diagram, add new blocks, temporarily hide certain blocks, move the position of certain blocks, modify selected blocks, clone one or more blocks to facilitate organization of the block diagram, highlight selected blocks, join two ore more blocks, change a graphical appearance of a component of a block diagram, for example, the color or thickness of lines in the block diagram, and/or perform the inverse of these operations. In one embodiment, the manipulation of the graphics, which can be useful for analysis of the model, does not change the underlying operation and connections between different components of the model or affect the simulation of the model. Alternatively, the manipulation of the graphical display produced by the viewer 564 may alter the underlying model 561.

Any suitable mechanism for allowing user to modify parameters and settings of a graphical object or component of a model, such as a block diagram, may be used in accordance with the teachings of the invention.

For example, according to an illustrative embodiment, the block diagram explorer 500 includes interface means for allowing the user to instruct the system 100 to modify the graphical attributes of the block diagram 540 displayed in pane 502, without modifying the actual components and underlying operation of the model. The illustrative interface means comprise buttons 522, 524, 526, 528, 592 and 594 or checkboxes 532, 534, 536, 538, 539, which the user selects using a mouse or other suitable selection means. One skilled in the art will recognize that any suitable means for receiving instructions from a user may be used, and that the invention is not limited to the illustrative method of inputting and receiving instructions from a user.

For example, the illustrative explorer includes a style pane 506, including a checkbox 532 for allowing a user to select a style for the displaying the block diagram model. The illustrative checkbox 532 allows a user to remove the reaction blocks from the model, leaving only the interconnected species blocks.

A generation selection pane 508 includes a hidden blocks checkbox 534 for allowing a user to instruct the system to show hidden blocks in generation and a show parents block 536 for allowing a user to instruct the system to display parent blocks of a selected block.

Figure 6A:
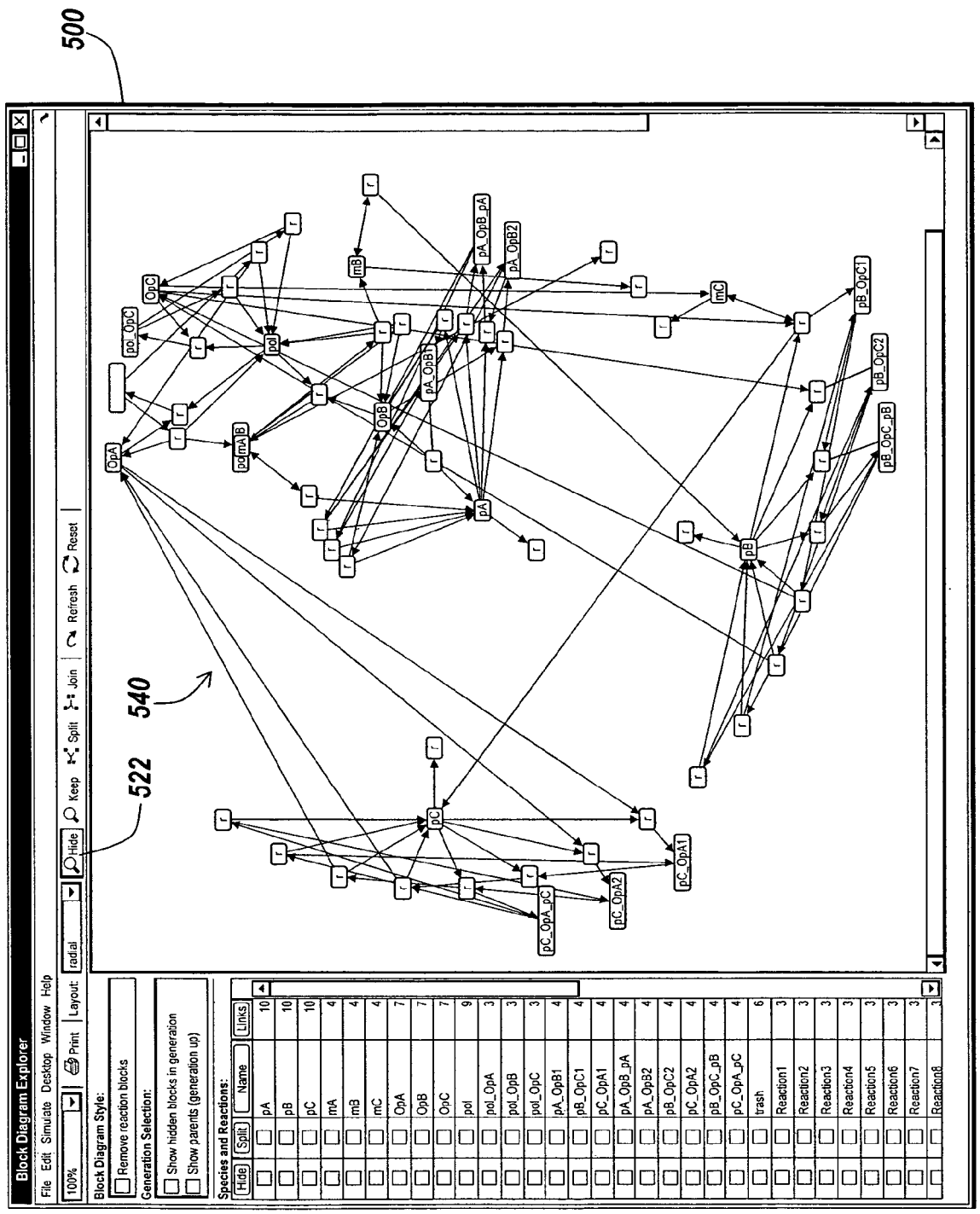
FIG. 6A is a screenshot of the block diagram explorer of FIG. 4 after a user has instructed the system to hide one of the blocks in the block diagram.

The hide button 522 of the illustrative block diagram explorer allows a user to select one or more blocks and instruct the system 100 to hide the selected blocks, i.e., remove the blocks from the block diagram, without removing the functionality of the hidden block from the model. For example, in the example shown in FIG. 6A, the user has selected the "trash" block 5420 and pressed the hide button 522 to remove the trash block from the diagram.

Alternatively, a selected block can be deleted entirely from the model, rather than being merely hidden from view.

Figure 6B:
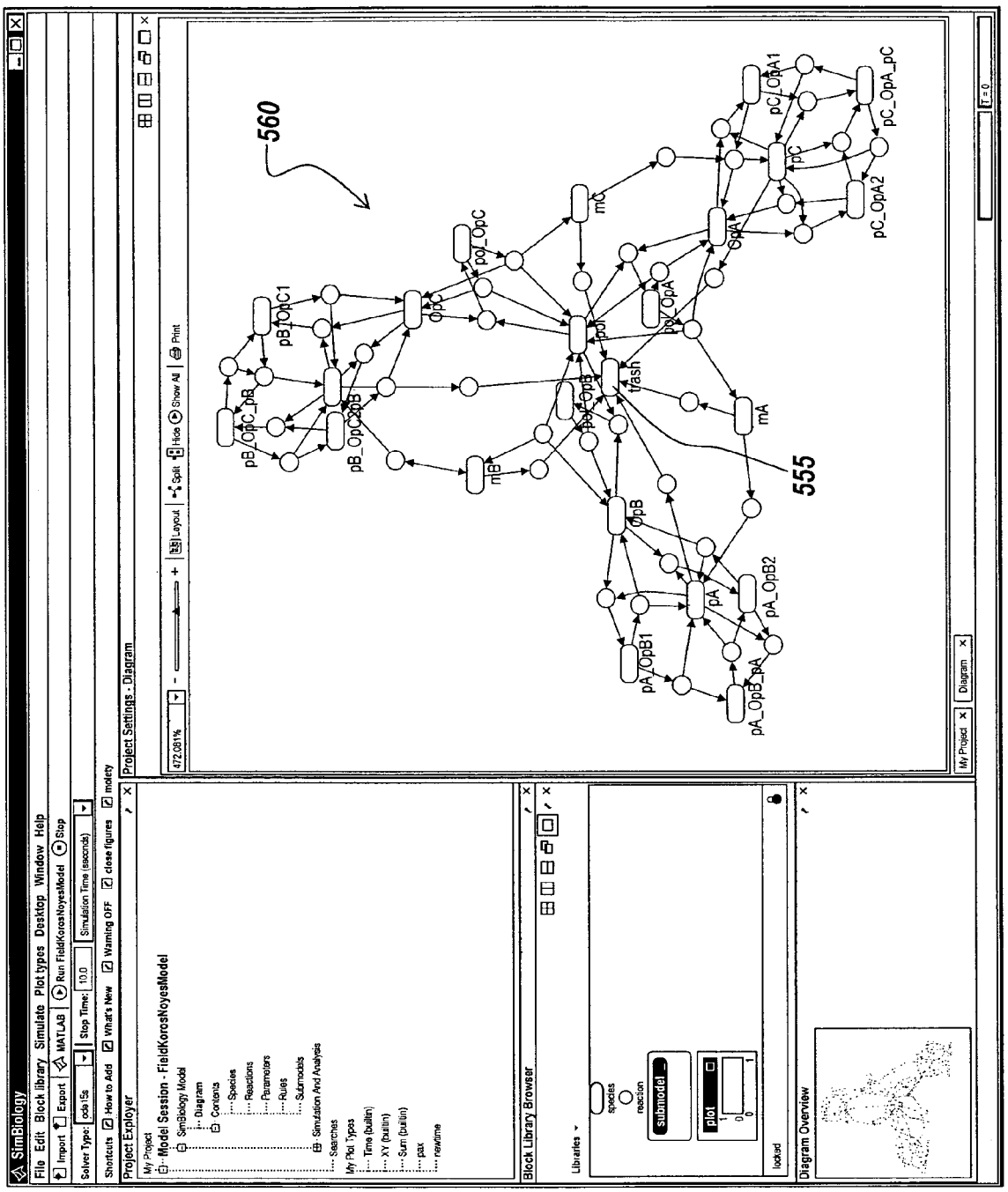
FIGS. 6B and 6C are block diagrams before and after one of the blocks in the block diagram is removed.
Figure 6C:
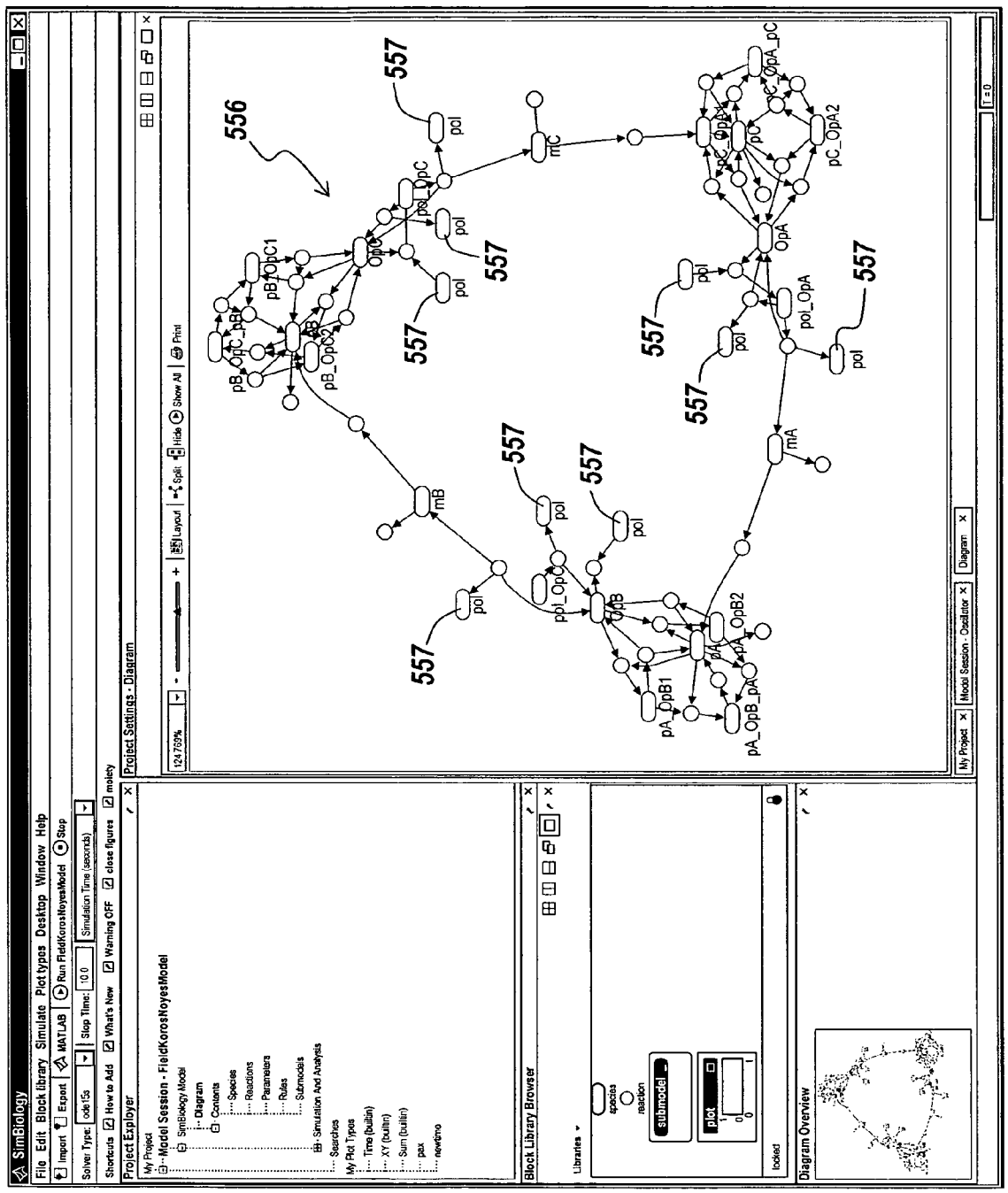

In the illustrative embodiment, the system removes the selected block or blocks and connecting arrows in response to the user instruction to hide the block, while all other components of the block diagram 540 remain in the previously-determined positions. Alternatively, the optimizer software that determines the position of the block diagram components can reorganize the blocks in a different format after one or more blocks are removed from the block diagram. For example, FIGS. 6B and 6C depict block diagram models 550 and 556 that show the dynamic layout of a block diagram model after a selected block is removed from the block diagram model. FIG. 6B is a block diagram model 550 before the selected block or blocks and connecting arrows are removed. The block diagram model includes the "trash" block 555, and the user may select the "trash" block 555 to remove. FIG. 6C is a block diagram model 556 after the selected "trash" block is removed. The illustrative embodiment may dynamically determine the position of the remaining block diagram components to reorganize the blocks in a different format after the selected "trash" block is removed. In this block diagram, the polymerase block is split into a plurality of cloned blocks 557. The block split will be described below in more detail with reference to FIG. 7.

The "hide" command may alternatively be executed by selecting one or more blocks using the hide checkboxes 538 associated with each block in the list pane 504. A hidden block may be brought back into view by deselecting a selected block in the hide checkboxes 538.

The keep button 524 allows a user to select one or more blocks to be kept in the block diagram, while removing unselected blocks from the block diagram 540. For example, if the user wants to remove a relatively large number of blocks, the user can select the blocks he wishes to keep in the block diagram. Then, the user selects the keep button 524 to instruct the modeling environment to remove all other blocks from the block diagram 540. The resulting block diagram of the biological or chemical system includes only those blocks selected by the user as "keep" blocks, while non-selected blocks are hidden.

Figure 7:
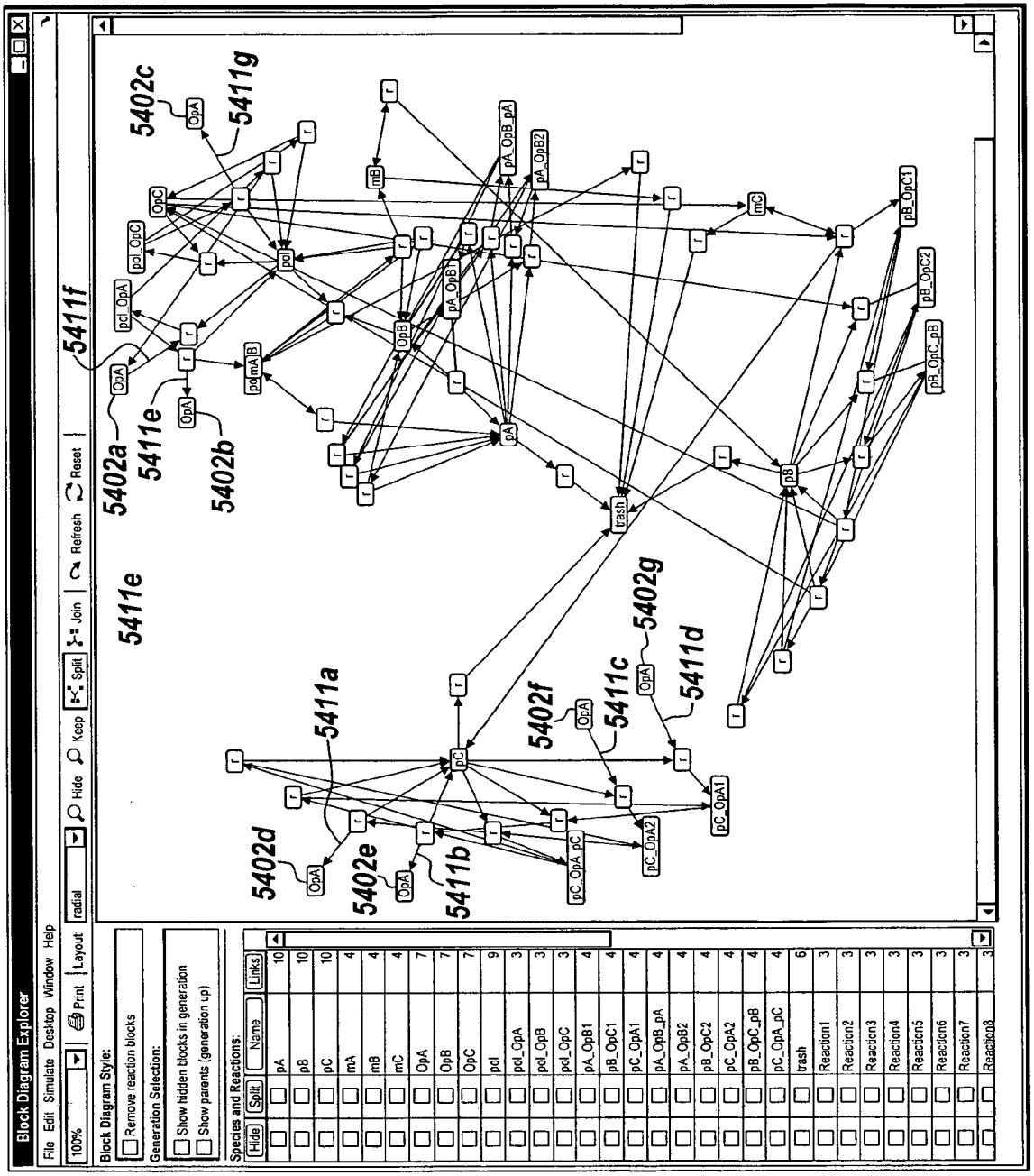
FIG. 7 is a screenshot of the block diagram explorer of FIG. 4 after a user has instructed the system to split one of the blocks in the block diagram.

The split button 526, when selected, instructs the system to split the graphical representation of a selected object into a plurality of blocks to aid in organization of the block diagram 540, without actually creating a new object in the model. The split command clones the graphical representation to create a plurality of cloned representations of the same object. For example, in the illustrative example shown in FIG. 4, the block 5402 representing the species OpA has a plurality of inputs and outputs, resulting in numerous arrows 5411a-5411g connecting to the OpA block 5402. The OpA block 5402 can be split by selecting the block and pressing the split button 526 to create a separate cloned block 5402a-5402g for each arrow going into or out of the block, as shown in FIG. 7. Each cloned block 5402a-5402g represents the same object, i.e., species OpA, and act in unison, so that when one cloned block is highlighted and manipulated, all related cloned blocks will also be highlighted and manipulated.

In the illustrative embodiment, the split command creates a separate cloned block for each link, i.e., for each arrow passing into and out of the selected block. According to an alternate embodiment of the invention, the split command can create subsets of cloned blocks, so that a cloned block can have a plurality of arrows extending into and out of the block. For example, all input arrows can pass to a first cloned block, while all outputs pass to a second cloned block.

The "split" command may alternatively be implemented by selecting one or more blocks using the split checkboxes 539 associated with each block in the list pane 504.

The join button 528 performs the inverse operation of the split command, i.e., joining cloned blocks into a single representation and connected all arrows to the single block. The "join" command may alternatively be implemented to join together the cloned representations into a single block by unselecting the checks in the checkboxes in the split column of the list pane 504.

A refresh button 592 and a reset button 594 are also provided for facilitating modification of the graphical parameters of the block diagram. The refresh button 592 may be used to update the display after the user selects an operation to be performed. Alternatively, the display can automatically update according to the user-defined instruction. The reset button 594 resets the block diagram to the original configuration.

Figure 8:
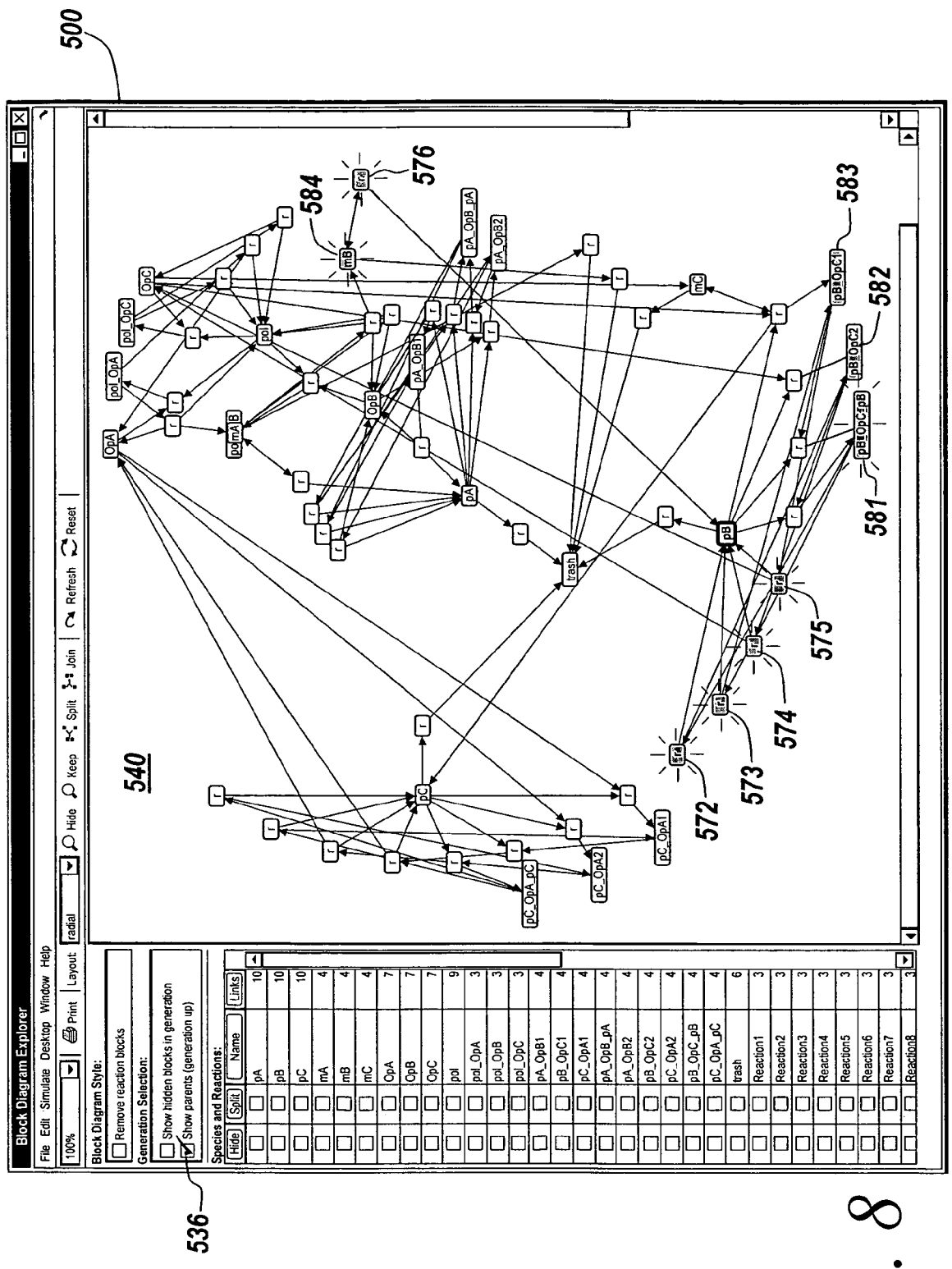
FIG. 8 is a screenshot of the block diagram explorer of FIG. 4 after a user has instructed the system to highlight parent blocks of a selected block in the block diagram.

FIG. 8 illustrates another application of the explorer 500 according to an embodiment of the invention. For a selected block, the user can instruct the system to show the next level of blocks in the hierarchy. For example, in FIG. 8, the user selects the pB species block 571 and requests the system to show the parent blocks, for example, by selecting checkbox 536. In response to the user request, the system can highlight or otherwise indicate the parent blocks i.e., the reactions that create the pB species. In the illustrative embodiment, the explorer 500 highlights reactions 572, 573, 574, 575 and 576, which utilize species 581, 582, 583, 584 to form the pB species. The "show parents" command can highlight only the reactions or can also highlight the species used by the reactions to produce the selected block. The explorer 500 can also highlight children blocks or blocks in the same generation as the selected block. In this manner, a user can walk up and down the hierarchy to analyze the system being modeled by the block diagram.

Figure 9A:
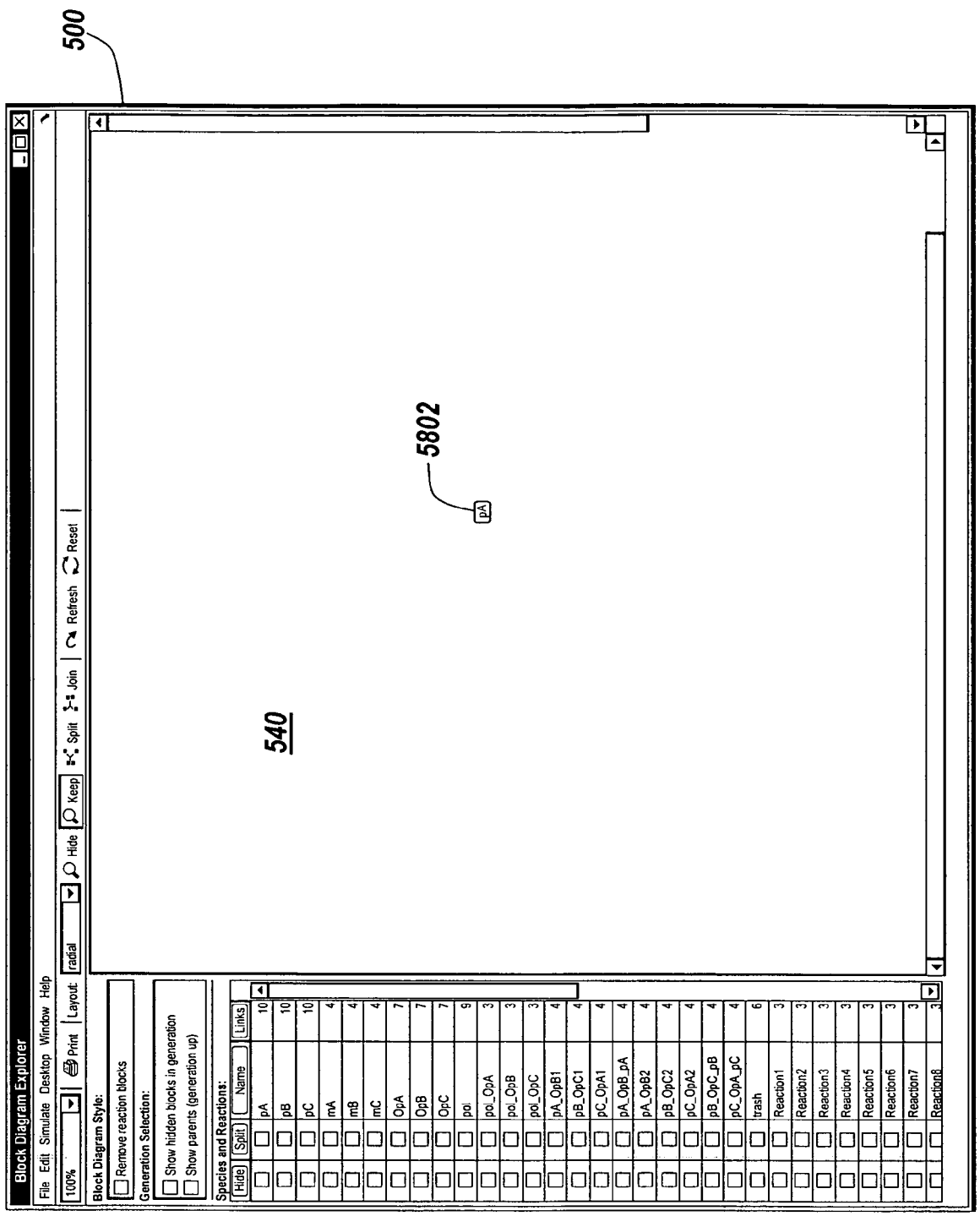
FIGS. 9A and 9B are a screenshot of the block diagram explorer of FIG. 4 as a user walks up the hierarchy of the block diagram.
Figure 9B:
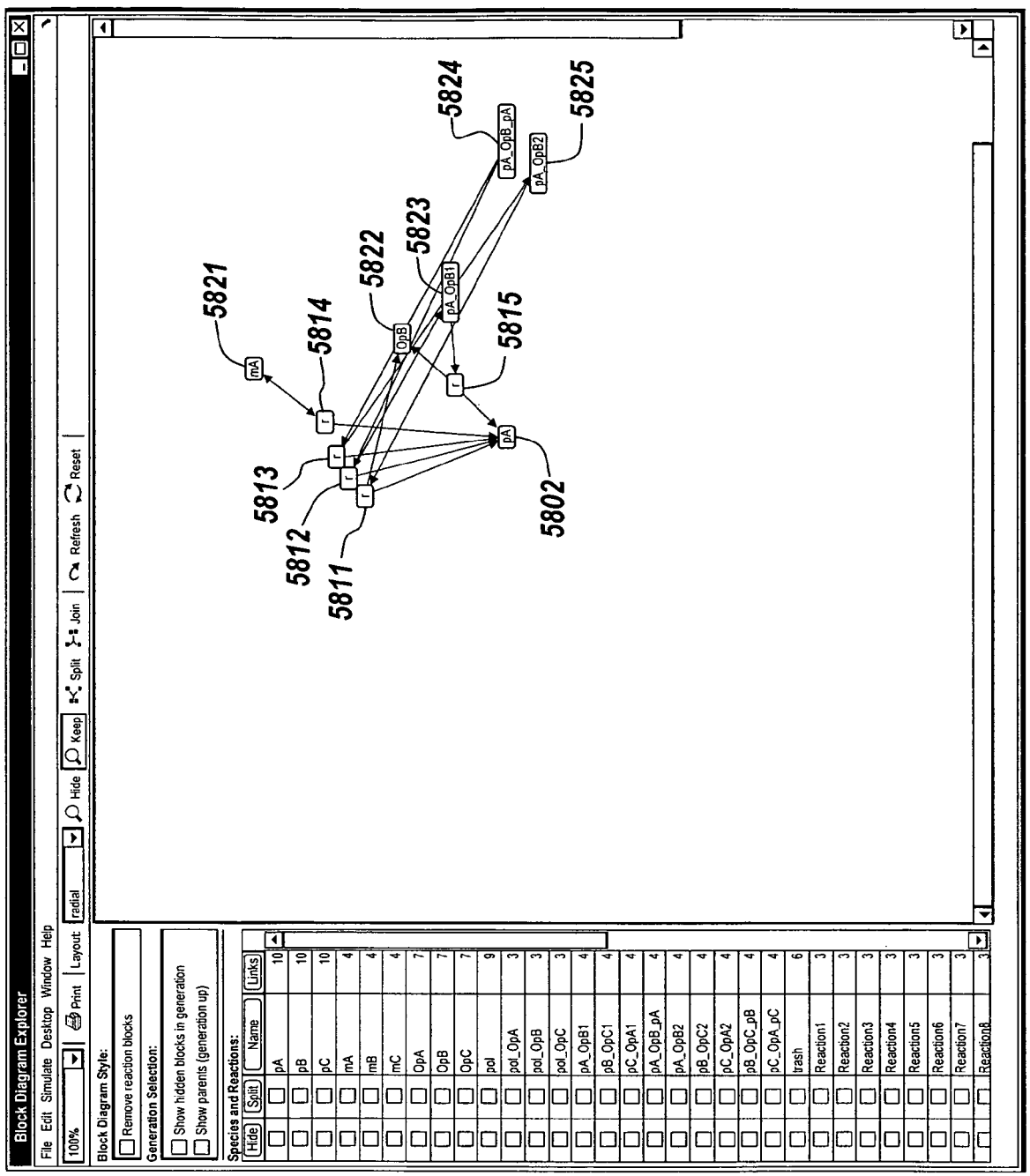

FIGS. 9A-9B illustrate still another example of an application of the block diagram explorer 500 according to an illustrative embodiment of the invention. As described above, a user can instruct the explorer 500 to keep a selected block while removing non-selected blocks from the block diagram display. In FIG. 9A, species pA, represented by block 5802 is kept, while all other blocks representing the biological or chemical are removed from the block diagram 540. The user can request the explorer to sequentially add different generations of blocks to the block diagram. For example, as shown in FIG. 9B, the explorer adds all parent blocks, including reaction blocks 5811, 5812, 5813, 5814, 5815, and species blocks 5821, 5822, 5823, 5824 and 5825, for the pA species back into the block diagram. The ability to remove and add entire generations of blocks at a time can provide further insight to the user regarding the system being modeled.

In another embodiment, the user may "pin" certain blocks in a selected position and move other blocks in the model to different locations.

While certain commands for manipulating the graphical display of a biological or chemical system have been described above, one skilled in the art will recognize that the invention is not limited to the illustrative commands or method of inputting the commands to the system regarding the graphical display.

Once a block diagram model has been constructed within a modeling environment 110 using the tools described above, the chemical or biological reaction may be simulated by executing the model. An execution engine carries out the task of compiling and linking the block diagram to produce an "in-memory executable" version of the model that is used for generating code and/or simulating a block diagram model. Execution of the block-diagram is also referred to as simulation. Model execution is carried out over a user-specified time span for a set of user-specified inputs.

The execution begins when the block diagram is compiled. The compile stage marks the start of model execution and involves preparing data structures and evaluating parameters, configuring and propagating block characteristics, determining block connectivity, and performing block reduction and block insertion. The preparation of data structures and the evaluation of parameters create and initialize basic data-structures needed in the compile stage.

For each of the blocks, a method forces the block to evaluate all of its parameters. This method is called for all blocks in the block diagram. If there are any unresolved parameters, execution errors are thrown at this point.

During the configuration and propagation of block and port/signal characteristics, the compiled attributes (such as dimensions, data types, complexity, or sample time) of each block (and/or ports) are setup on the basis of the corresponding functional attributes and the attributes of blocks (and/or ports) that are connected to the given block through lines. The attribute setup is performed through a process during which block functional attributes "ripple through" the block diagram from one block to the next following signal connectivity. This process (referred to herein as "propagation"), serves two purposes. In the case of a block that has explicitly specified its block (or its ports' functional attributes, propagation helps ensure that the attributes of this block are compatible with the attributes of the blocks connected to it. If not, an error is issued. Secondly, in many cases blocks are implemented to be compatible with a wide range of attributes. Such blocks adapt their behavior in accordance with the attributes of the blocks connected to them. This is akin to the concept of polymorphism in object-oriented programming languages. The exact implementation of the block is chosen on the basis of the specific block diagram in which this block finds itself. Included within this step are other aspects such as validating that all rate-transitions within the model yield deterministic results and that the appropriate rate transition blocks are being used.

The compilation step also determines actual block connectivity. In this step, the virtual blocks in the block diagram, which play no semantic role in the execution of a block diagram, are optimized away (removed) and the remaining non-virtual blocks are reconnected to each other appropriately. This compiled version of the block diagram with actual block connections is used from this point forward in the execution process. The way in which blocks are interconnected in the block diagram does not necessarily define the order in which the equations (methods) corresponding to the individual blocks will be solved (executed). The actual order is partially determined during the sorting step in compilation. Once the compilation step has completed, the sorted order cannot be changed for the entire duration of the block diagram's execution.

Following the compilation stage is the model link stage. After linking has been performed, code may or may not be generated. If code is generated, the model is simulated/executed through accelerated simulation mode in which the block diagram model (or portions of it) is translated into either software modules or hardware descriptions (broadly termed code). If this stage is performed, then the stages that follow use the generated code during the execution of the block diagram. If code is not generated, the block diagram may execute in interpretive mode in which the compiled and linked version of the block diagram may be directly utilized to execute the model over the desired time-span. This interpretive mode of execution is suitable for getting fine-grained signal traceability. There are several different advantages to execution through code generation. Execution of generated code can be more efficient than interpretive execution because of fewer data-structures and lesser internal messaging in the engine, although the increased efficiency generally comes at the cost of decreased execution traceability. Simulation of hardware descriptions during execution can help identify and resolve bugs in the software stage of a design project. Such bugs prove much more expensive to track and fix once the system has been implemented in hardware. Additionally, block diagram modeling software can be integrated with other software environments that are suitable for modeling and simulating special classes of systems. Models can be tested directly in hardware thereby making prototyping of new systems fast and cost-effective. Those skilled in the art will recognize that when users generate code, they may choose to not proceed further with the block diagram's execution. They may choose to take the code and deploy it outside of the confines of the modeling software environment. This is normally the last step in the design of dynamic systems in a block diagram software package.

In one particular embodiment the modeling environment 110 provides a tool allowing a user to select the complexity with which a model executes. Referring back to FIG. 3B as an example, a user can be provided with a choice of executing pathway 4100 as a simple input-output block or executing pathway 4100 in the more detailed form shown in FIG. 3B.

Referring back to FIG. 1, the model created in the modeling environment 110 can be used by the simulation engine 120 to perform a simulation. Dynamic systems, such as biological processes and chemical reactions, are typically modeled as sets of differential, difference, algebraic, and/or recursive equations. At any given instant of time, these equations may be viewed as relationships between the system's output response ("outputs"), the system's input stimuli ("inputs") at that time, the current state of the system, the system parameters, and time. The state of the system may be thought of as a numerical representation of the dynamically changing configuration of the system. For instance, in a physical system modeling a simple pendulum, the state may be viewed as the current position and velocity of the pendulum. Similarly, a signal-processing system that filters a signal would maintain a set of previous inputs as the state. The system parameters are the numerical representation of the static (unchanging) configuration of the system and may be viewed as constant coefficients in the system's equations. For the pendulum example, a parameter is the length of pendulum and for the filter example; a parameter is the values of the filter taps. A simulation engine useful in connection with the present invention is SIMULINK®, available from The MathWorks, Inc, of Natick, Mass.

Types of mathematical models used in the study of dynamic systems include differential equations, difference equations, algebraic equations, and hybrid models. For modeling biological processes and chemical reactions, a stochastic model may be useful. This model describes systems using stochastic techniques, such as Gillespie, Gibson/Bruck, and τ-leaping.

For example, the Gillespie stochastic technique uses an algorithm to numerically simulate the time evolution of a given chemical system. In the Gillespie technique, reaction events given selected probabilities of occurring, and the events which occur change the probabilities of subsequent events. The algorithm determines, for a system in a given state, the next reaction to occur and the time that the next reaction occurs using probability. The algorithm is based on a quantity $P(t,u)$, which is the probability that a reaction u will occur at the time interval t. The probabilities are based on the classical rate coefficients (k), the volume of the container, which can be a cell, a partition of a cell, a compartment of the cell, such as the nucleus or other organelles, or other container, and the concentration of reactants in a given reaction. Once a time and reaction have been computed, the method carries out the reaction, i.e., it updates the state of the system to reflect the transformation of reactants into products, then increments the time by t and determines another reaction to occur and when the reaction will occur. The Gillespie technique is described in detail in the article: Gillespie, D. T. 1977, *Exact Stochastic Simulation of Coupled Chemical Reactions*, Journal of Physical Chemistry, vol. 81, pp. 2340-2361.

The Gibson/Bruck stochastic technique is a variation of the Gillespie algorithm and described in the journal article Gibson, M. A., and J. Bruck, *Efficient Exact Stochastic Simulation of Chemical Systems with Many Species and Many Channels,* 2000 Journal of Physical Chemistry A, vol. 104, pp. 1876-1889.

One skilled in the art will recognize that any suitable stochastic technique for simulating the time evolution of a given chemical system may be utilized in the present invention. These techniques are useful when the continuous approximation implied by ODE/DAE systems is not applicable. This may be the case when dealing with small molecule counts, such as RNA polymerase binding to DNA to transcribe a particular gene. An example of a chemical equation that could be treated stochastically is shown in the reactions table of FIG. 2B, e.g., s32+Dnak→s32:Dnak. This equation indicates that one molecule of s32 bonds with one molecule of Dnak. When simulated stochastically, this reaction occurs at a random time determined according to a probability distribution associated with that reaction. The reaction time may be determined by drawing a random number from the probability distribution.

Inherent in four of the classes of systems (ODE, difference equations, algebraic equations and composite) is the notion of system sample time. The sample-time is the time interval at which the inputs, state, or outputs (collectively referred to as the results) of the system are traced as time progresses. Based on sample times, a system can be described as a discrete-time system, continuous-time system and hybrid system. Stochastic systems may occur at a random time determined by a reaction-specific operative probability distribution.

A discrete-time system is a system in which the evolution of the system results is tracked at finite intervals of time. In the limit as the interval approaches zero, the discrete-time system becomes a continuous-time system. The intervals of time may be periodic or non-periodic. Sometimes, non-periodic rate systems, such as stochastic systems, are referred to as non-uniform rate systems meaning that there is no periodic rate at which the response can be tracked. A continuous-time system is a system in which the evolutions of the system results are continuously changing. Continuous-time signals change during numerical integration. An example of a continuous-time system is one described by an ODE. There can also be algebraic or composite continuous-time systems. A hybrid system is a system with both discrete-time and continuous-time elements.

As noted previously, stochastic reactions occur at a random time based on an operative probability distribution, which do not neatly fit either a fixed-step type of solver or a continuous-time solver. In order to adequately model systems including stochastic reactions, either alone or as part of a hybrid system including both stochastic and either fixed-solver elements or variable-solver elements, the following steps may be taken.

Figure 10:
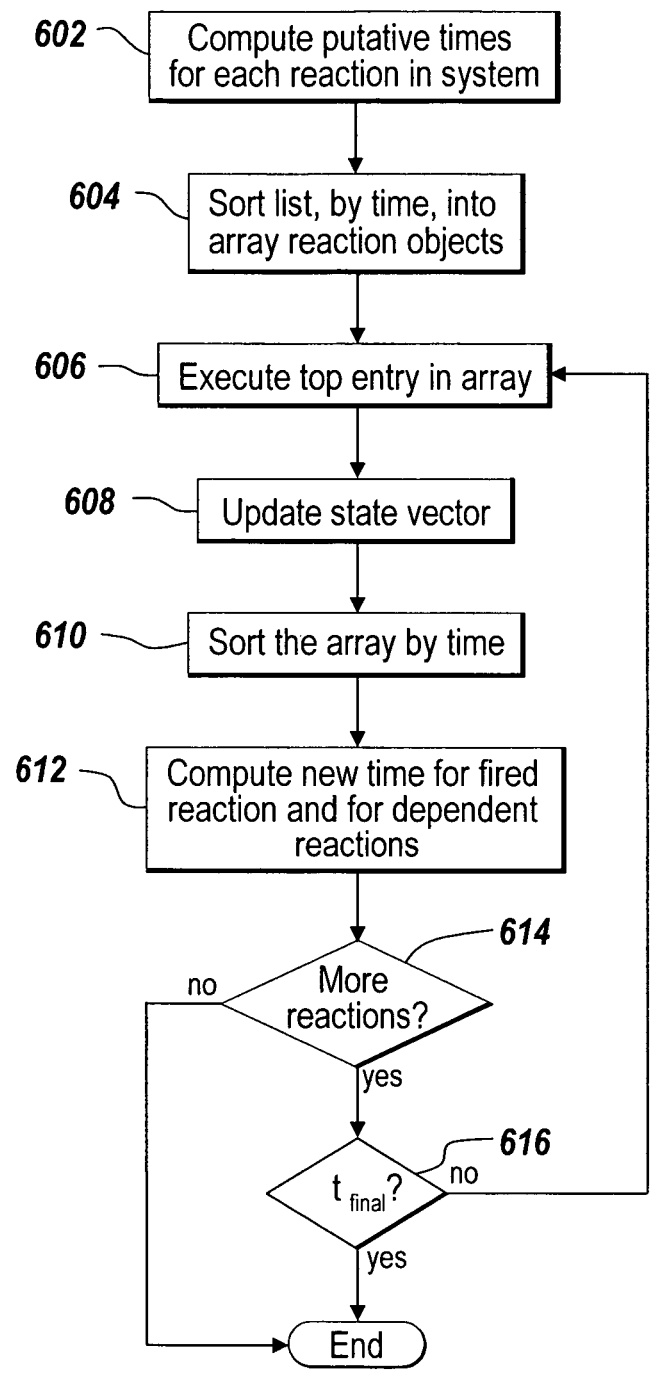
FIG. 10 is a flowchart depicting one embodiment of the steps taken to simulate a modeled biological process or chemical reaction using the stochastic solver method.

FIG. 10 illustrates the steps involved in simulating a biological or chemical system modeled using the modeling environment 100. In a first step, the simulation determines putative times for each reaction in the model (step 602). In one embodiment, a reaction time for a selected reaction is selected by drawing a random numbers from a reaction distribution, such as an exponential distribution, though one skilled in the art will recognize that any suitable means for determining a reaction time for a reaction in a model may be used according to the teachings of the invention.

Once putative reactions times are computed for each reaction in the system, the times are sorted, by putative occurrence time, into a state array (step 604). In one embodiment, the state array is an array of pointers sorted by occurrence time, each of the pointers pointing to the object to be executed at that point in model simulation. Once sorted, the object identified by the first entry in the array is executed (step 606).

Because execution of the top object may affect the amount of species present in the modeled system or the putative reaction times for specific reactions in the table, the putative time for each of the entries in the state array is recalculated (step 608) and the state array is resorted (step 610).

The simulation engine 120 checks for additional reactions to execute (step 614). If additional reactions exist, the simulation engine 120 checks to determine in the final simulation time has been reached (step 616). If not, the simulation engine 120 executes the next entry in the state array (step 606). Otherwise, the simulation terminates. One skilled in the art would recognize that other scheduling methodologies may be used.

As described above, the results generated by the simulation engine 120 may be used by the layout/view optimizer 563 in the modeling environment to determine the rules for determining the layout topology of the graphical model. For example, the layout/view optimizer could place all blocks with a high flux or high energy in the middle of the model, to minimize clutter.

Referring again to FIG. 1, the results generated by the simulation engine 120 may be used by an analysis environment 130. In other embodiments, the analysis environment 130 operates directly on a model, for example, to generate a steady-state value for a modeled system instead of simulating the system. In some of these embodiments, the analysis tool 120 does this by setting the derivative of all differential equations to 0 and solving the system algebraically. In others of these embodiments, the analysis engine performs a flux-balance analysis, as is known in the art, to determine the steady-state value of a system. Other well-known forms of analysis that may be employed by the analysis environment 120 include using non-linear solvers, sensitivity analysis, bifurcation analysis, parameter scans, parameter estimation and network inference analysis. The result of these analyses may be provided to the simulation engine 120 as input for its calculations.

The analysis environment 130 may further process the results generated by the simulation engine 120 or it may display the results visually or auditorially. For example, the analysis environment 120 may use graph visualization techniques to identify to a user similar pathways. In some embodiments the analysis environment 130 interfaces with data acquisition hardware (not shown in FIG. 1) which allows the analysis environment 130 to compare the generated results with experimental data. In these embodiments, data gathered from an ongoing experiment is used to correct or generate a model of the reaction that is occurring in situ. In some embodiments the experiment is conducted on a microarray or a gene chip. For example, if the existence of a given protein is predicted by a model but data acquired from the experiment indicates that the protein does not exist, the analysis tool 130 may signal a user, either auditorially or visually, that the in-situ experiment and the predicted response differ. For embodiments in which the experiment is conducted on a microarray, the gathered data may differ between microwells. In these embodiments, the analysis tool may average the value of the gathered data. In others of these embodiments, the analysis environment 130 may signal a difference if the data from a single microwell differs from the model's predicted response. In some embodiments, the amount of tolerable difference between the in situ experiment and the predicted result is user-configurable. In other embodiments, the analysis tool transmits the gathered data to the modeling environment 110 so that the model may be modified to account for the difference. In still other embodiments, the analysis environment 130 graphically displays the expected result of the experiment and data gathered from the experiment.

In other embodiments, the data acquisition hardware allows the analysis tool to control an experiment that is in progress based on the results generated by the simulation engine 120. These embodiments may be useful in construction of nanomachinery. In these embodiments, a model may call for insitu temperature to be at 102 degrees Fahrenheit. If a thermocouple measuring temperature of the in situ environment indicates that the temperature has fallen below 102 degrees Fahrenheit, more heat may be applied to the experiment.

Data acquisition hardware may include any of a number of hardware devices compatible with the computing platform executing the integrated modeling, simulation, and analysis environment 100. For example, in embodiments in which the environment 100 executes on a personal computer, the data acquisition hardware interfaces with the local system bus 220. In embodiments such as those shown in FIG. 2B, the data acquisition hardware interfaces with the HyperTransport bus, Rapid I/O bus, or InfiniBand. The data acquisition hardware can communicate with instruments and experiments that use GPIB (IEEE-488, HPIB), VISA, TCP/IP, and UDP standards.

Although the systems and methods of the present invention have been described above as executing on a single machine, they may also be used in a client-server environment such as X-Windows or Microsoft Terminal Services. The modeling environment 110, simulation engine 120, and analysis environment 130 may each execute on separate machines, or they may be aggregated in any combination between machines. For example, in one particular embodiment, the modeling environment 110 and the analysis environment0 130 execute on a "client" machine while the simulation engine executes on a "server" machine. In these embodiments, the computers may be connected via a number of network topologies including bus, star, or ring topologies. The network can be a local area network (LAN), a metropolitan area network (MAN), or a wide area network (WAN) such as the Internet. The respective computers may connect to the network 180 through a variety of connections including standard telephone lines, LAN or WAN links (e.g., T1, T3, 56 kb, X.25), broadband connections (ISDN, Frame Relay, ATM), and wireless connections. Connections can be established using a variety of communication protocols (e.g., TCP/IP, IPX, SPX, NetBIOS, NetBEUI, SMB, Ethernet, ARCNET, Fiber Distributed Data Interface (FDDI), RS232, IEEE 802.11, IEEE 802.11a, IEE 802.11b, IEEE 802.11g and direct asynchronous connections).

An embodiment of the present invention relates to a computer storage product including a computer-readable medium having computer code thereon for performing various computer-implemented operations. The media and computer code may be those specially designed and constructed for the purposes of the present invention, or they maybe of the kind well known and available to those having skill in the computer software arts. Examples of computer-readable media include, but are not limited to: magnetic media such as hard disks, floppy disks, and magnetic tape; optical media such as CD-ROMs, CD-R/RW discs, DVD-ROMs, DVD-RAMs, and holographic devices; magneto-optical media such as floptical disks; solid-state memories such as flash drives, memory sticks, xD cards, MultiMedia cards, and Smart Media cards; and hardware devices that are specially configured to store and execute program code, such as application-specific integrated circuits ("ASICs"), field-programmable gate arrays (FPGAs), programmable logic devices ("PLDs"), read only memories ("ROMs"), random access memories ("RAMs"), erasable programmable read only memories ("EPROMs"), and electrically erasable programmable read only memories ("EEPROMs").

Examples of computer code that may be embodied on such computer-readable media include machine code, such as produced by a compiler, and files containing higher level code that are executed by a computer using an interpreter. For example, an embodiment of the invention may be implemented using Java, C++, or other object-oriented programming language and development tools.

While the present invention has been described with references to various specific embodiments, it should be understood by those skilled in the art that various changes may be made and equivalents substituted without departing manufactured by the spirit and scope of the invention defined by the appended claims. In addition, modifications may be made to adapt to a particular situation, material, composition of matter, method, process, series of steps to the objective of the present invention while staying within the spirit and scope of the invention and such modifications are intended to be within the scope of the appended claims. In particular, while the methods disclosed have been described with reference to particular steps in a particular order, it will be understood that these steps may be combined, sub-divided, or reordered to form an equivalent method without departing manufactured by the teachings of the present invention. Accordingly, unless specifically indicated herein, the order and grouping of steps is not a limitation of the present invention.

The invention claimed is:

1. A method comprising:
providing, using a computing device, a matrix listing a plurality of species participating in one or more chemical reactions;
generating, using the computing device, an executable block diagram based on the matrix, where:
the executable block diagram represents a system including the one or more chemical reactions,
the executable block diagram includes:
a plurality of blocks representing the plurality of species, and
a plurality of lines representing a relationship among the plurality of species,
executing the executable block diagram simulates the one or more chemical reactions,
the generating includes:
processing, using the computing device, the matrix to determine an optimized two-dimensional position for the plurality of blocks on a graphical layout of the executable block diagram based on the relationship among the plurality of species;
dynamically displaying, on a display device, the graphical layout of the executable block diagram in a graphical user interface, where the plurality of blocks are displayed at the determined optimized two-dimensional position;
receiving, using the computing device, an input to modify the graphical layout of the executable block diagram; and
modifying, using the computing device, the graphical layout of the executable block diagram based on the received input.

2. The method of claim 1, wherein the modifying is in response to a user request.

3. The method of claim 1, wherein the modifying is performed automatically.

4. The method of claim 1, further comprising:
creating the executable block diagram based on a simulation result for a model of the system, wherein the modifying is based on the simulation result.

5. The method of claim 1, further comprising:
creating the executable block diagram based on an analysis of a model of the system, wherein the modifying is based on the analysis.

6. The method of claim 1, wherein the modifying comprises:
selecting one or more of the plurality of blocks in the executable block diagram; and
removing non-selected blocks from the executable block diagram.

7. The method of claim 6, further comprising:
recalculating a position of remaining blocks in the executable block diagram after removing the non-selected blocks.

8. The method of claim 6, further comprising:
re-adding the non-selected blocks to the executable block diagram, in response to a user request.

9. The method of claim 1, wherein the modifying comprises:
selecting one or more of the plurality of blocks; and
hiding the selected one or more of the plurality of blocks.

10. The method of claim 9, further comprising:
recalculating a position of remaining blocks in the executable block diagram after removing the selected one or more of the plurality of blocks.

11. The method of claim 1, wherein the modifying comprises:
selecting one of the plurality of blocks; and
splitting the selected one of the plurality of blocks into a plurality of cloned blocks.

12. The method of claim 11, wherein the modifying comprises:
joining a plurality of cloned blocks into a single block.

13. The method of claim 1, wherein the modifying comprises:
selecting a block and highlighting adjacent blocks in the executable block diagram.

14. The method of claim 13, wherein the adjacent blocks comprise a parent block for the selected block.

15. The method of claim 13, wherein the adjacent blocks comprise a child block for the selected block.

16. The method of claim 2, wherein the user request is input by selecting a button associated with a graphical parameter in the graphical user interface.

17. The method of claim 2, wherein the user request is input by selecting a checkbox associated with a graphical parameter in the graphical user interface.

18. The method of claim 1, further comprising modifying a model of the system used to create the executable block diagram based on the modification to the graphical layout.

19. The method of claim 1, wherein the modifying comprises modifying a rule in a layout/view optimizer used to determine the position of the plurality of blocks in the executable block diagram.

20. A non-transitory computer readable medium storing instructions that, when executed by a processor, cause the processor to:
provide a matrix listing a plurality of species participating in one or more chemical reactions;
generate an executable block diagram based on the matrix, where:
the executable block diagram represents a system including the one or more chemical reactions,
the executable block diagram includes:
a plurality of blocks representing the plurality of species, and
a plurality of lines representing a relationship among the plurality of species,
executing the executable block diagram simulates the one or more chemical reactions,
the generating includes:
processing the matrix to determine an optimized two-dimensional position for the plurality blocks on a graphical layout of the executable block diagram based on the relationship among the plurality of species;
dynamically display the graphical layout of the executable block diagram in a graphical user interface, where the plurality of blocks are displayed at the determined optimized two-dimensional position;
receive an input to modify the graphical layout of the executable block diagram; and
modify the graphical layout of the executable block diagram based on the received input.

21. A method comprising:
providing, using a computing device, a matrix listing a plurality of species participating in one or more chemical reactions;
generating, using a computing device, an executable block diagram based on the matrix, where:
the executable block diagram represents a system including the one or more chemical reactions,
the executable block diagram includes:
a plurality of blocks representing the plurality of species, and
a plurality of lines representing a relationship among the plurality of species,
executing the executable block diagram simulates the one or more chemical reactions;
the generating includes:
processing, using the computing device, the matrix to determine an optimized two-dimensional position for the plurality of blocks on a graphical layout of the executable block diagram based on the relationship among the plurality of species;
dynamically displaying, on a display device, the graphical layout of the executable block diagram in a graphical user interface, where the plurality of blocks are displayed at the determined optimized two-dimensional position;
receiving, using the computing device, an instruction from a user regarding a graphical parameter of the graphical layout of the executable block diagram; and
modifying, using the computing device, the graphical layout of the executable block diagram according to the instruction.

22. The method of claim 21, wherein the modifying comprises one of adding, removing, splitting, joining and highlighting a selected block in the executable block diagram.

23. The method of claim 22, further comprising recalculating a position of remaining blocks in the executable block diagram after the modifying.

24. The method of claim 21, wherein the instruction from the user is input to the electronic device by selecting one of a button and a checkbox associated with the graphical parameter in the graphical user interface.

25. A non-transitory computer readable medium storing instructions that, when executed by a processor, cause the processor to:
provide a matrix listing a plurality of species participating in one or more chemical reactions;
generate an executable block diagram based on the matrix, where:
the executable block diagram represents a system including the one or more chemical reactions,
the executable block diagram includes:
a plurality of blocks representing the plurality of species, and
a plurality of lines representing a relationship among the plurality of species,
executing the executable block diagram simulates the one or more chemical reactions,
the generating includes:
processing the matrix to determine an optimized two-dimensional position for the plurality of blocks on a graphical layout of the executable block diagram based on the relationship among the plurality of species;

dynamically display the graphical layout of the executable block diagram in a graphical user interface, where the plurality of blocks are displayed at the determined optimized two-dimensional position;

receive an instruction from a user regarding a graphical parameter of the graphical layout of the executable block diagram; and modify the graphical layout of the executable block diagram according to the instruction.

26. A system comprising:

a processor for executing instructions to provide:
  a block diagram explorer for:
    providing a matrix listing a plurality of species participating in one or more chemical reactions,
  a modeling component comprising:
    a modeling environment for generating an executable block diagram using the matrix, where:
      the executable block diagram represents a system including the one or more chemical reactions,
      the executable block diagram includes:
        a plurality of blocks representing the plurality of species, and
        a plurality of lines representing a relationship among the plurality of species,
      executing the executable block diagram simulates the one or more chemical reactions,
      the generating includes:
        processing the matrix to determine an optimized two-dimensional position for the plurality of blocks on a graphical layout of the executable block diagram based on the relationship among the plurality of species,
  a display device dynamically displaying the graphical layout in a graphical user interface, where the plurality of blocks are displayed at the determined optimized two-dimensional position; and
  a simulation engine accepting as input the executable block diagram and generating as output dynamic behavior of the system represented by the executable block diagram.

27. The method of claim 1, further comprising:

creating the matrix listing the plurality of species participating in the one or more chemical reactions, wherein each column of the matrix corresponds to one species and each row of the matrix corresponds to one species, such that number of rows of the matrix and number of columns of the matrix is equal to number of species.

28. The method of claim 1, wherein the executable block diagram includes at least one block representing at least one of the one or more chemical reactions.

* * * * *

UNITED STATES PATENT AND TRADEMARK OFFICE
CERTIFICATE OF CORRECTION

| | |
|---|---|
| PATENT NO. | : 8,543,337 B2 |
| APPLICATION NO. | : 11/408723 |
| DATED | : September 24, 2013 |
| INVENTOR(S) | : Ricardo E. Paxson et al. |

It is certified that error appears in the above-identified patent and that said Letters Patent is hereby corrected as shown below:

In the Specification

Column 2, line 23, change "and" to --as--.

Signed and Sealed this
Twenty-fifth Day of March, 2014

Michelle K. Lee
*Deputy Director of the United States Patent and Trademark Office*